US011970684B2

(12) United States Patent
Skerlos et al.

(10) Patent No.: US 11,970,684 B2
(45) Date of Patent: Apr. 30, 2024

(54) BIOREACTOR INSERT AND BIOFILM SUPPORT, RELATED APPARATUS AND RELATED METHODS

(71) Applicant: THE REGENTS OF THE UNIVERSITY OF MICHIGAN, Ann Arbor, MI (US)

(72) Inventors: Steven Skerlos, Ann Arbor, MI (US); Lutgarde Raskin, Ann Arbor, MI (US); Timothy Fairley-Wax, Ann Arbor, MI (US); Nishant Jalgaonkar, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 18/153,689

(22) Filed: Jan. 12, 2023

(65) Prior Publication Data
US 2023/0159876 A1    May 25, 2023

Related U.S. Application Data

(63) Continuation of application No. 17/277,910, filed as application No. PCT/US2019/053801 on Sep. 30, 2019, now Pat. No. 11,591,559.
(Continued)

(51) Int. Cl.
*C12M 1/00* (2006.01)
*C02F 3/10* (2023.01)
(Continued)

(52) U.S. Cl.
CPC .............. *C12M 29/26* (2013.01); *C02F 3/10* (2013.01); *C02F 3/1268* (2013.01);
(Continued)

(58) Field of Classification Search
CPC ...... C12M 29/26; C12M 23/06; C12M 25/00; C12M 27/14; C12M 33/14; C02F 3/10;
(Continued)

(56) References Cited

U.S. PATENT DOCUMENTS 4,940,540 A     7/1990  McDowell
4,978,616 A *  12/1990  Dean, Jr. ................. C12M 25/20
                                                         435/813
(Continued)

FOREIGN PATENT DOCUMENTS

CN       202063910 U    12/2011
CN       104045170 A     9/2014
(Continued)

OTHER PUBLICATIONS

Water Environment Federation, Treatment Intensification for Resource Recovery: Advances in Granules and Membrane Bioreactor Technologies, pp. 40-52 (Dec. 5, 2018).
(Continued)

*Primary Examiner* — William H. Beisner
*Assistant Examiner* — Danielle B Henkel
(74) *Attorney, Agent, or Firm* — MARSHALL, GERSTEIN & BORUN LLP

(57) ABSTRACT

The disclosure relates to bioreactors, for example for biological treatment and, more specifically to bioreactor insert apparatus including biofilms and related methods. The bioreactor insert apparatus provides a means for circulation of reaction medium within the bioreactor, a biofilm support, and biological treatment of an inlet feed to die reactor/insert apparatus. The bioreactor insert apparatus has a high relative surface area for biofilm attachment and is capable of generating complex flow patterns and increasing treatment efficiency/biological conversion activity in a biologically-active reactor. The high surface area structure incorporates
(Continued)

multiple biofilm support structures such as meshes at inlet and outlet portions of the structure. The biofilm support structures and biofilms thereon can increase overall reaction rate of the bioreactor and/or perform some solid/liquid separation in the treatment of the wastewater or other influent.

32 Claims, 10 Drawing Sheets

Related U.S. Application Data

(60) Provisional application No. 62/739,447, filed on Oct. 1, 2018.

(51) Int. Cl.
*C02F 3/12* (2023.01)
*C02F 3/28* (2023.01)
*C12M 1/12* (2006.01)
*C12M 1/26* (2006.01)
*C12M 3/06* (2006.01)
*C12P 5/02* (2006.01)

(52) U.S. Cl.
CPC .......... *C02F 3/2806* (2013.01); *C02F 3/2853* (2013.01); *C12M 23/06* (2013.01); *C12M 25/00* (2013.01); *C12M 27/14* (2013.01); *C12M 33/14* (2013.01); *C12P 5/023* (2013.01)

(58) Field of Classification Search
CPC .... C02F 3/1268; C02F 3/2806; C02F 3/2853; C12P 5/023
See application file for complete search history.

(56) References Cited

U.S. PATENT DOCUMENTS

| | | | |
|---|---|---|---|
| 5,656,494 A * | 8/1997 | Kant | B01D 53/85 435/297.1 |
| 5,733,454 A | 3/1998 | Cummings | |
| 8,017,384 B2 * | 9/2011 | Tsai | C12M 23/44 435/297.5 |
| 8,058,058 B2 * | 11/2011 | Hickey | C12M 25/10 210/321.79 |
| 2008/0248552 A1 * | 10/2008 | Castillo Fernandez | C12M 23/34 435/243 |
| 2010/0240094 A1 | 9/2010 | Gantefort et al. | |
| 2015/0368131 A1 | 12/2015 | Garrido Fernandez et al. | |
| 2018/0237734 A1 | 8/2018 | Uller | |
| 2021/0309955 A1 | 10/2021 | Skerlos et al. | |

FOREIGN PATENT DOCUMENTS

| | | |
|---|---|---|
| DE | 69718464 T2 | 10/2003 |
| WO | WO-86/02944 A1 | 5/1986 |
| WO | WO-2017/174093 A2 | 10/2017 |

OTHER PUBLICATIONS

International Application No. PCT/US2019/053801, International Search Report and Written Opinion, dated Dec. 11, 2019.
Buntner, A. et al., "Three stages MBR (methanogenic, aerobic biofilm and membrane filtration) for the treatment of low-strength wastewaters", *Water Sci. Technol.*, 64.2:397-402 (2011).
Ersahin, M.E. et al., "A review on dynamic membrane filtration: Materials, appications and future perspectives", *Bioresour. Technol.*, 122:196-206 (2012).
Daigger, G.T., "Evolving Urban Water and Residuals Management Paradigms: Water Reclamation and Reuse, Decentralization, and Resource Recovery", *Water Environ. Res.*, 81(8):809-23 (2009).
Guan, D. et al., "Pilot trial study of a compact macro-filtration membrane bioreactor process for saline wastewater treatment", *Water Sci. Technol.*, 70.1:120-26 (2014).
Guan, D. et al., "Changes in the physical properties of the dynamic layer and its correlation with permeate quality in a self-forming dynamic membrane bioreactor", *Water Res.*, 140:67-76 (2018).
Hu, Y. et al., "Anaerobic dynamic membrane bioreactor (AnDMBR) for wastewater treatment: A review", *Bioresour. Technol.*, 247:1107-18 (2018).
Lei, Z. et al., "Application of anaerobic membrane bioreactors to municipal wastewater treatment at ambient temperature: a review of achievements, challenges, and perspectives", *Bioresour. Technol.*, https:/doi.org/10.1016/j.biortech.2018.07.050 pp. 1-50 (2018).
Leng, L. et al., "A review on the bioenergetics of anaerobic microbial metabolism close to the thermodynamic limits and its implications for digestion applications", *Bioresour. Technol.*, http://dx.doi.org/10.1016/j.biortech.2017.09.103 pp. 1-12 (2017).
Li, Y. et al., "Potentially direct interspecies electron transfer of methanogenesis for syntrophic metabolism under sulfate reducing conditions with stainless steel", *Bioresour. Technol.*, 234:303-09 (2017).
Lin, H. et al., "A review on anaerobic membrane bioreactors: Applications, membrane fouling and future perspectives", *Desalination*, 314:169-188 (2013).
Lovley, D. R., "Happy together: microbial communities that hook up to swap electrons", *ISME Journal*, 11:327-336 (2017).
McCarty, P. L. et al., "Domestic Wastewater Treatment as a Net Energy Producer—Can This be Achieved?", *Environ. Sci. Technol.*, 45:7100-06 (2011).
Ozgun, H. et al., "A review of anaerobic membrane bioreactors for municipal wastewater treatment: Integration options, limitations and expectations", *Sep. Purif. Technol.*, 118:89-104 (2013).
Shin, C. et al., "Current status of the pilot-scale anaerobic membrane bioreactor treatments of domestic wastewaters: A critical review", *Bioresour. Technol.*, 247:1038-46 (2018).
Skouteris, G. et al., "Anaerobic membrane bioreactors for wastewater treatment: A review", *Chem. Eng. J.*, 198-199:138-48 (2012).
Smith, A. L. et al., "Perspectives on anaerobic membrane bioreactor treatment of domestic wastewater: A critical review", *Bioresour. Technol.*, 122:149-59 (2012).
Smith, A.L. et al., Anaerobic membrane bioreactor treatment of domestic wastewater at psychrophilic temperatures ranging from 15 °C to 3 °C, *Environ. Sci. Water Res. Technol.*, 1:56-64 (2015).
Smith, A. L. et al., "Navigating Wastewater Energy Recovery Strategies: A Life Cycle Comparision of Anaerobic Membrane Bioreactor and Conventional Treatment Systems with Anaerobic Digestion", *Environ. Sci. Technol.*, 48:5972-81 (2014).
Smith, A. L. et al., "Membrane biofilm development improves COD removal in anaerobic membrane bioreactor wastewater treatment", *Microb. Biotechnol.*, 8:883-894 (2015).
Wang, Y.- K et al., "A pilot investigation into membrane bioreactor using mesh filter for treating low-strength municipal wastewater", *Bioresour. Technol.*, 122:17-21 (2012).
Xie, Z. et al., "An anaerobic dynamic membrane bioreactor (AnDMBR) for landfill leachate treatment: Performance and microbial community identification", *Bioresour. Technol.*, 161:29-39 (2014).
European Patent Application No. 19868276.7, Extended European Search Report, dated Jun. 15, 2022.

* cited by examiner

BIOREACTOR INSERT AND BIOFILM SUPPORT, RELATED APPARATUS AND RELATED METHODS

CROSS-REFERENCE TO RELATED APPLICATIONS

This is a continuation of U.S. application Ser. No. 17/277,910 (filed Mar. 19, 2021; now U.S. Pat. No. 11,591,559), which is a National Stage of International Application No. PCT/US19/53801 (filed Sep. 30, 2019; incorporated herein by reference in its entirety), which claims priority to U.S. Provisional Application No. 62/739,447 (filed Oct. 1, 2018), which is incorporated herein by reference in its entirety.

STATEMENT OF GOVERNMENT INTEREST

This invention was made with government support under CBET-1604069 awarded by the National Science Foundation and under CBET-1133793 awarded by the National Science Foundation. The government has certain rights in the invention.

FIELD OF THE DISCLOSURE

The present disclosure relates to bioreactors, for example for biological treatment and, more specifically to bioreactor insert apparatus including biofilms and related methods.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Membrane bioreactors (MBRs) are used in a wide array of filter applications. MBRs combine microbial processes in a bioreactor containing diverse microbial communities or specific microorganisms with a membrane barrier that filters out the microorganisms from the water in the bioreactor.

MBRs, which employ microfiltration or ultrafiltration membranes, have attracted considerable attention in the wastewater treatment industry due to their ability to produce a high-quality effluent at reasonable hydraulic retention times (HRTs), and anaerobic MBRs (AnMBRs) also produce energy in the form of biogas. However, even AnMBRs are not currently advantageous for treatment of low to medium strength wastewater relative to current high rate activated sludge (aerobic) systems which employ anaerobic treatment of sludge, from net energy usage and net global warming impact perspectives. Two major drawbacks such as high energy requirement for membrane fouling mitigation and expensive membrane modules, which limit the scale at which MBRs can be applied, are solved by shifting to dynamic membrane bioreactors (DMBRs). This is because DMBRs employ coarser meshes (larger pore size than the membranes used in MBRs) made from materials such as nylon, silk, or stainless steel which are less energy intensive to clean and much cheaper to produce. Additionally, DMBRs can operate at higher fluxes than MBRs, which means that low HRTs (high loading rates), which are essential to achieve high methane yields during anaerobic treatment of low to medium strength wastewater, can be achieved with even smaller physical footprint. Current DMBRs employ a similar membrane configuration to conventional MBRs (i.e., a tubular or flatsheet membrane in a submerged or external side-stream configuration), and thus also have significant global warming impact, largely due to dissolved methane in reactor effluent. Dynamic membranes are typically applied in continually stirred tank reactors (CSTRs) or upflow anaerobic sludge blanket reactors (UASBs), and the system relies on biological treatment performance in the reactor and any additional treatment from the biofilm that forms on the mesh (referred to as a dynamic membrane). Previous studies with AnMBRs have shown that biofilms become increasingly important for organics removal relative to the biomass in suspension in the bioreactor as wastewater temperature decreases. Similarly, biofilms in aerobic MBRs are also important for treatment when high quality effluents are needed. Adequate treatment results have already been achieved by both aerobic and anaerobic DMBRs in lab settings, and now at pilot-scale for treatment of both low and high strength wastewaters. Currently, there are not any commercial dynamic membrane modules, and all studies have used self-made modules.

CN104045170A discloses a sewage treatment device based on 3D printing of biological biofilm carrier media. The apparatus includes plastic biofilm carrier media that is specifically designed to have a large surface area and a roughness so that biofilm adhesion is faster. The 3D-printed media is suspended in the reactor which treats wastewater. The design uses 3D printing technology to enhance surface area and allow biofilm formation for treatment of wastewater.

SUMMARY

The disclosed apparatus incorporates structures and flow arrangements to harness more biofilm treatment activity than conventional systems, in particular because biofilm activity is increasingly significant (e.g., relative to activity of suspended microorganisms) for removal/conversion of various compounds as temperature decreases for both anaerobic biofilms (e.g., used for wastewater treatment) and aerobic biofilms. For example, biofilm activity assists in organics removal, nutrient removal, removal of other specific contaminants, increasing product yield such as in a fermentation application, etc. In an anaerobic application, the disclosed apparatus also shifts methane production away from membrane biofilms on (bioreactor-external) permeating membranes to lower effluent dissolved methane concentrations. The present disclosure provides techniques for treating aqueous waste streams at high volumetric and/or organic loading rates by removing various compounds (e.g., organic or otherwise), while minimizing dissolved methane in the permeate in the case of anaerobic treatment, in particular using an anaerobic bioreactor incorporating a bioreactor insert apparatus as disclosed herein. These techniques are able to reduce net greenhouse gas emissions and increase recoverable energy.

The disclosed bioreactor insert apparatus has a high relative surface area, for example relative to the insert apparatus volume and/or the overall bioreactor reaction volume, which apparatus is capable of generating complex flow patterns and increasing treatment efficiency/biological conversion activity in a biologically-active reactor. The high surface area structure (e.g., a 3D-printed structure) incorporates multiple biofilm support structures (e.g., meshes such as conductive meshes) at inlet and outlet portions of the structure. The biofilm support structures are configured to operate as a biofilm attachment medium such that, during operation of the insert apparatus in combination with a bioreactor, the biofilm support structures and biofilms thereon can increase overall reaction rate of the bioreactor (e.g., increased net biological activity) and/or perform some solid/liquid separation in the treatment of the wastewater or other influent. The disclosed insert apparatus with high relative surface area, when placed into a bioreactor or in fluid communication with a bioreactor, is known as a dynamic membrane bioreactor (DMBR). Such bioreactors are well-suited to handle waste/wastewater streams from municipalities and a variety of industries including agriculture, dairy, food and beverage, and paper.

By promoting biofilm growth on a support or conductive mesh, mass transfer limitations are reduced and microbial interactions between microorganisms are increased, for example syntrophic microorganisms and methanogens. Further, biofilm growth not only increases treatment efficiency but additionally, for anaerobic applications, maximizes methane production in the bulk of the reactor, thereby maximizing overall methane recovery and minimizing permeate dissolved methane concentrations. Namely, methane produced at locally high concentrations (e.g., substantially above equilibrium methane-in-water concentrations for the reactor operating temperature) is provided with substantial residence time in the reactor to equilibrate with and be released into the reactor gas headspace, where the methane can be desirably recovered as a product instead of being lost via the permeate (which is an environmental pollutant in addition to a reduction in product yield). Further still, to boost the hydrolysis and methanogenesis rates at psychrophilic temperatures, the biofilm supports and corresponding biofilms on the insert apparatus in the bioreactor more generally provide substantially increased surface area for biofilm-based biological activity and conversion.

As opposed to biofilms growing on typical media inserted within a suspended growth bioreactor system, a biofilm on a support within the bioreactor or on a membrane in an external membrane filtration unit (MFU) experiences a reduction in mass transfer limitations when water passes through (e.g., a mesh biofilm support) or is forced through (e.g., a MFU membrane). This reduction in mass transfer limitation (i.e. increase in mass transfer) enhances biological activity of the biofilm. Furthermore, direct interspecies electron transfer ("DIET") between microorganisms as a means to transport redox intermediates between one-another is of specific interest for systems designed to exploit biofilms, in particular with electrically conductive biofilm supports or meshes, as this type of transfer enables microorganisms to directly exchange electrons via a conductive surface. Such direct electron transfer minimizes chemical energy losses leaving more energy for microbial growth and subsequent methane production.

In one aspect, the disclosure relates to a bioreactor insert apparatus for reaction medium circulation, biofilm support, and biological treatment, the apparatus comprising: an inlet volume in fluid communication with a first fluid inlet; an outlet volume in fluid communication with a first fluid outlet; a plurality of exit volumes, each exit volume being in (direct or indirect) fluid communication with the inlet volume and comprising at least one exit biofilm support disposed at a boundary between the exit volume and an external volume outside the bioreactor insert apparatus, wherein: the exit biofilm support (e.g., mesh) is adapted to promote growth, attachment, and metabolism of microorganisms or microbes in the form of a biofilm thereon, and the exit biofilm support is adapted to permit fluid and solid transport across the exit biofilm support and between the exit volume and the external volume; and a plurality of recirculation volumes, each recirculation volume being in (direct or indirect) fluid communication with the outlet volume and comprising at least one recirculation biofilm support disposed at a boundary between the recirculation volume and the external volume outside the bioreactor insert apparatus, wherein: the recirculation biofilm support (e.g., mesh) is adapted to promote growth, attachment, and metabolism of microorganisms or microbes in the form of a biofilm thereon, and the recirculation biofilm support is adapted to permit fluid and solid transport across the recirculation biofilm support and between the exit volume and the external volume. In various embodiments, a ratio (ANA) for the insert apparatus of total surface area (A) of all biofilm supports combined (i.e., on all exit volumes and recirculation volumes) to bioreactor insert apparatus volume ($V_A$), including total from inlet volume (e.g., cylinder), outlet volume (e.g., annulus), exit volumes (e.g., exit tubes), and recirculation volumes (e.g., recirculation tubes) can be at least 1 $m^{-1}$ (or equivalently 1 $m^2/m^3$ as a specific surface area parameter).

Various embodiments of the disclosed bioreactor insert apparatus are possible.

In an embodiment, the bioreactor insert apparatus is a single (unitary) structure comprising the inlet volume, the outlet volume, the plurality of exit volumes, and the plurality of recirculation volumes. In a particular embodiment, the inlet volume is defined by a cylindrical tube in fluid communication with the first fluid inlet; the outlet volume is defined by an annular tube around the cylindrical tube in fluid communication with the first fluid outlet; the exit volumes are defined by (cylindrical) exit tubes in fluid communication with the cylindrical tube inlet volume; and the recirculation volumes are defined by (cylindrical) recirculation tubes in fluid communication with the annular tube outlet volume.

In an embodiment, the bioreactor insert apparatus comprises: a first (inlet) structure comprising the inlet volume and the plurality of exit volumes mounted thereto; and a second (outlet) structure comprising the outlet volume and the plurality of recirculation volumes mounted thereto. The first structure and the second structure are separate structures with the exit volumes being in fluid communication with the recirculation volumes via the external volume.

In an embodiment, the first fluid outlet is in fluid communication with the first fluid inlet.

In an embodiment, the apparatus comprises at least 10 exit volumes.

In an embodiment, the apparatus comprises at least 10 recirculation volumes.

In an embodiment, the biofilm support is in the form of a mesh.

In an embodiment, the biofilm support comprises an electrically conductive material (e.g., as a mesh or otherwise).

In an embodiment, one or more of the insert apparatus and the biofilm support comprises an electrically resistive material (e.g., as a mesh or otherwise).

In an embodiment, the bioreactor insert apparatus or at least one component thereof (e.g., biofilm supports or meshes) has been formed by a 3D printing process.

In an embodiment, the bioreactor insert apparatus further comprises biofilms adhered to the biofilm supports (e.g., during operation of the insert apparatus and/or corresponding bioreactor). The biofilms can comprise a diverse range of microorganisms, for example a community of microorganisms collectively having biological activity.

In an embodiment, the bioreactor insert apparatus further comprises a biofilm seed adhered to the biofilm support. The biofilm seed can comprise a water-soluble adhesive matrix and a community of microorganisms as a biofilm precursor distributed throughout the matrix.

In another aspect, the disclosure relates to a bioreactor comprising: a (closed or open) reaction vessel defining an interior reaction volume; and a bioreactor insert apparatus mounted within the reaction vessel. The bioreactor insert apparatus comprises: an inlet volume in fluid communication with a first fluid inlet; an outlet volume in fluid communication with a first fluid outlet; a plurality of exit volumes, each exit volume being in fluid communication with the inlet volume and comprising at least one exit biofilm support disposed at a boundary between the exit volume and an external volume outside the bioreactor insert apparatus, wherein: the exit biofilm support is adapted to promote growth, attachment, and metabolism of microorganisms in the form of a biofilm thereon, and the exit biofilm support is adapted to permit fluid and solid transport across the exit biofilm support and between the exit volume and the external volume; and a plurality of recirculation volumes, each recirculation volume being in fluid communication with the outlet volume and comprising at least one recirculation biofilm support disposed at a boundary between the recirculation volume and the external volume outside the bioreactor insert apparatus, wherein: the recirculation biofilm support is adapted to promote growth, attachment, and metabolism of microorganisms in the form of a biofilm thereon, and the recirculation biofilm support is adapted to permit fluid and solid transport across the recirculation biofilm support and between the exit volume and the external volume. The external volume of the bioreactor insert apparatus corresponds to a portion of the interior reaction volume outside the bioreactor insert apparatus.

Various embodiments of the disclosed bioreactor are possible, for example including the bioreactor insert apparatus in any of its variously disclosed embodiments.

In an embodiment, a ratio ($A/V_A$) of total surface area (A) of all biofilm supports combined to bioreactor insert apparatus volume ($V_A$) is at least 1 m$^{-1}$.

In an embodiment, the bioreactor insert apparatus is rotatably mounted within the reaction vessel.

In an embodiment, the bioreactor further comprises a bioreactor gas outlet in fluid communication with a headspace portion of the interior reaction volume.

In an embodiment, the bioreactor further comprises attachment media for microbial growth, for example which media are suspended in a corresponding aqueous reaction medium during operation of the bioreactor.

In an embodiment, the bioreactor further comprises a membrane filtration unit comprising: a separation membrane, a membrane inlet in fluid communication with the first fluid outlet and a first (retentate) side of the separation membrane, a membrane retentate outlet in fluid communication with the first fluid inlet and the first (retentate) side of the separation membrane, and a membrane permeate outlet in fluid communication with a second (permeate; opposing) side of the separation membrane. The membrane filtration unit can be external to the bioreactor reaction vessel.

In another aspect, the disclosure relates to a method for forming a bioreactor product (e.g., methane), the method comprising: providing a bioreactor and bioreactor insert apparatus according to any of their variously disclosed embodiments, wherein: the bioreactor insert apparatus further comprises biofilms adhered to the biofilm supports, the biofilms having biological (e.g., methanogenic) activity, an aqueous reaction medium at least partially fills the interior reaction volume and the bioreactor insert apparatus, and suspended microorganisms are present in the aqueous reaction medium; feeding an influent stream (e.g., wastewater influent) comprising one or more organic constituents or other reactants for conversion to the bioreactor insert apparatus via the first fluid inlet; circulating the influent stream through the inlet volume, into the exit volumes, through the exit biofilm supports and biofilms thereon, into the external volume, through the recirculation biofilm supports and biofilms thereon, into the recirculation volumes, into the outlet volume, and through the first fluid outlet; and converting the one or more influent organic constituents or other reactants to a (methane) product, in particular by biofilm activity and/or suspended microorganism activity.

Various embodiments of the disclosed method are possible, for example including the bioreactor insert apparatus and/or bioreactor in any of their variously disclosed embodiments.

In an embodiment, at least 50%, 65%, or 80% of total microorganisms in the bioreactor are incorporated into the biofilms.

In an embodiment, the biofilms have methanogenic activity. In a further embodiment, aqueous fluid removed through the first fluid outlet comprises dissolved methane at a concentration in a range of 50% to 150% relative to the equilibrium concentration of methane in water.

In an embodiment, the biofilms comprise a community of anaerobic microorganisms (e.g., collectively having methanogenic activity and/or fermentative activity).

In an embodiment, the biofilms comprise a community of aerobic microorganisms (e.g., collectively having nitrifying activity).

In an embodiment, the biofilms comprise a community of anoxic microorganisms (e.g., collectively having denitrifying activity).

In an embodiment, the biofilms comprise a community of aerobic, anoxic, and/or anaerobic microorganisms (e.g., collectively having activities of relevance for different redox conditions).

In various embodiments, the method comprises operating the bioreactor at a temperature in a range of 1° C. to 20° C. (e.g., a psychrophilic temperature), in a range of 20° C. to 40° C. (e.g., a mesophilic temperature), or in a range of 40° C. to 60° C. (e.g., a thermophilic temperature).

In an embodiment, the bioreactor further comprises attachment media for microbial growth suspended in the aqueous reaction medium.

In an embodiment, the method comprises operating the bioreactor at a hydraulic retention time (HRT) in a range of 2 hr to 40 hr.

While the disclosed apparatus, methods, and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

Figure 1:
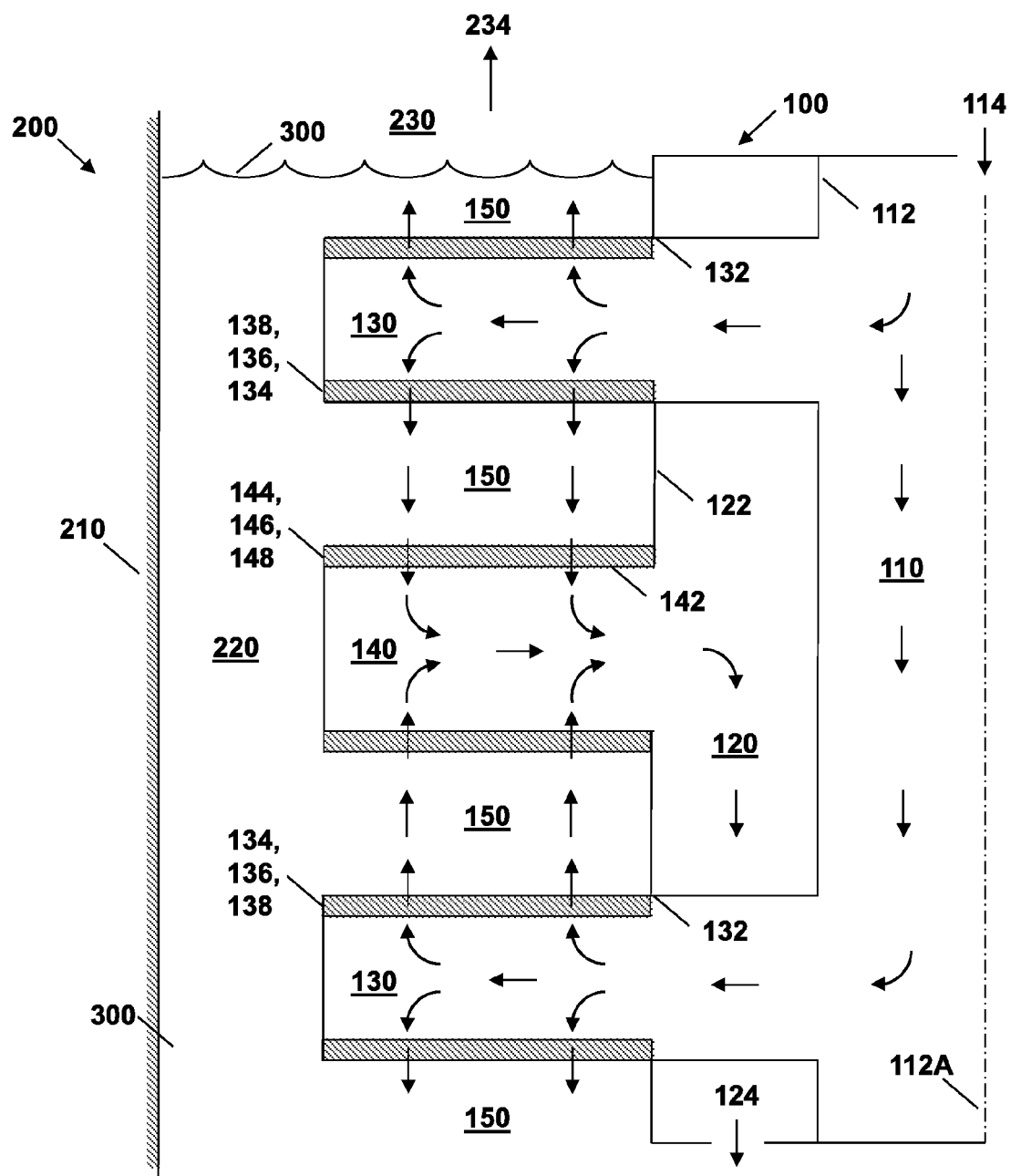
FIG. 1 illustrates a bioreactor insert apparatus and corresponding bioreactor according to the disclosure, which apparatus and bioreactor can treat aqueous wastewater comprising organic components by sending the wastewater through multiple exit and recirculation volumes in series separated by meshes or supports that serve for biofilm attachment.
Figure 2:
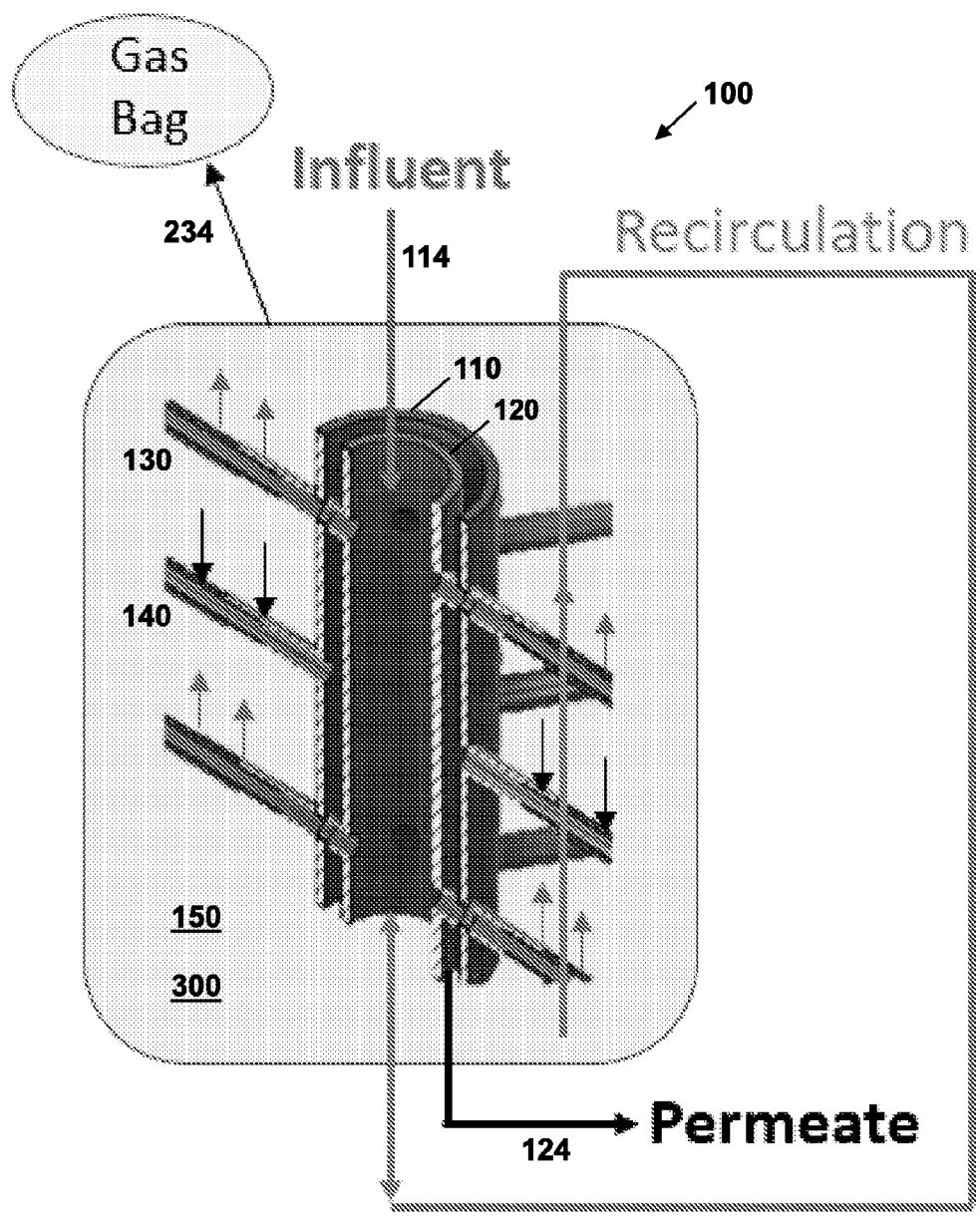
FIG. 2 is a cut-away perspective view of a bioreactor insert apparatus according to the disclosure.

An illustrative embodiment of a bioreactor insert apparatus according to the disclosure is shown in the figures, discussed in the examples, and described in more detail below. The illustrative embodiment includes a 3D-printed structure with (stainless steel) mesh supports for biofilm formation thereon, which are attached to influent (or recirculating) and permeating (or exit) branches of the biofilm support structure to efficiently treat waste/wastewater streams and which can aid in biogas production in anaerobic applications. The stainless steel meshes act as a platform for biofilm growth. Additionally, in anaerobic systems, stainless steel or other metallic/electrically conductive materials for the meshes facilitate transfer of electrons between syntrophic and methanogenic microorganisms, resulting in favorable thermodynamics which lead to increased organics removal and methane production. The bulk liquid of the reactor is continuously recirculated so that the wastewater is forced through the biofilm on the influent and permeating branches many times during its residence time in the reactor and so that microorganisms develop a robust biofilm on the influent and permeating meshes. Periodically, the recirculation direction can be reversed so that not all the microorganisms accumulate inside and/or outside of the biofilm structure. The biofilms on the influent and permeating branches generally can have one or both of biological activity for product formation and some degree of solid/liquid separation. The influent branch dynamic membrane biofilms are highly active as they are responsible for the majority of the organics removal, and they provide some barrier to solids transport. Consequently, in anaerobic systems, they will produce the majority of methane via methanogens. The dynamic membrane biofilm that forms on the permeating meshes can be primarily responsible for retaining solids in the reactor and provides additional organics removal, thus providing a more substantial barrier to solids transport and some biological activity for further product formation. This can be useful as it lessens the solids loading in the outlet stream of the insert apparatus, which could be directed to a membrane filtration unit for final permeate clarification. In the illustrative embodiment in the examples, the total biofilm support/biofilm membrane area is over 1,000 cm$^2$ for a structure height of 0.2 meters. Some attached microbial growth may occur on the 3D-printed structure itself, but due to the designed flow pattern, the majority of biofilm will develop on the meshes. In typical operation, transmembrane pressure (TMP) of the system can be monitored and periodic backwashing can be employed when the TMP reaches a designated threshold, for example at or below 60 kPa to prevent biofilm breakdown (e.g., a threshold TMP of 5, 10, 20, 30, 40, 50, or 60 kPa TMP below which the reactor would normally operate and above which backwashing can be implemented to reduce TMP). Suitably, the reaction system can be normally operated at a TMP in a range of 0.01 kPa to 20 kPa (e.g., at least 0.01, 0.1, or 1 kPa and/or up to 5, 8, 10, 15, or 20 kPa), with periodic backwashing or other cleaning when the TMP reaches or exceeds the designated threshold. By harnessing biofilm treatment on influent (or exit) and permeating (or recirculation) branches, and by utilizing inexpensive, coarse membrane material, the disclosed bioreactor insert apparatus can produce excellent quality effluent with low capital and operating costs.

The present disclosure generally relates to a bioreactor insert apparatus 100 and corresponding bioreactor 200, for example as illustrated in FIGS. 1-5. The bioreactor insert apparatus 100 provides a means for circulation of reaction medium 300 within the bioreactor 200, a biofilm support, and biological treatment of an inlet feed to the reactor 200/insert apparatus 100.

Figure 5:
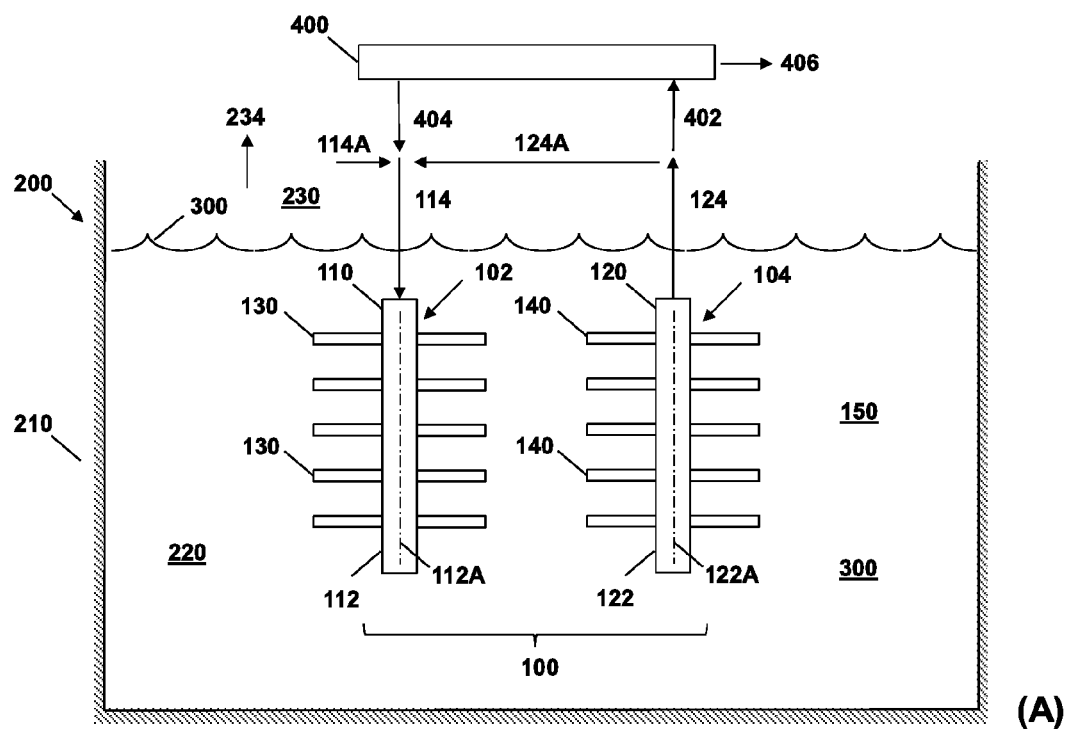
FIG. 5 illustrates a bioreactor insert apparatus and corresponding bioreactor according to the disclosure in an embodiment in which the insert apparatus has separate influent and effluent structures. Panel (A) illustrates an embodiment with the influent and effluent structures in the same bioreactor vessel. Panel (B) illustrates an embodiment with the influent and effluent structures in separate bioreactor vessels that collectively define the bioreactor.
Figure 5:
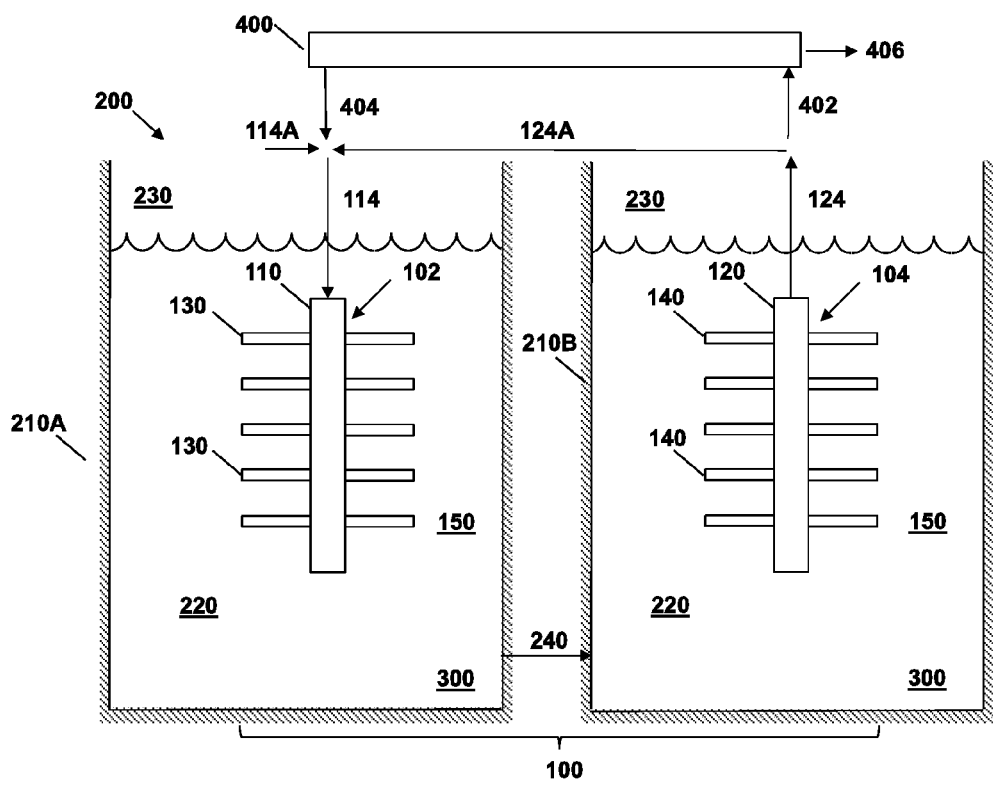

The insert apparatus 100 includes an inlet volume 110 in fluid communication with a first fluid inlet 114 and an outlet volume 120 in fluid communication with a first fluid outlet 124. The first fluid inlet 114 can be an inlet to the bioreactor 200 including the insert apparatus 100 therein, such that feed (e.g., wastewater or otherwise) initially enters the insert apparatus 100 before entering the bioreactor reaction medium 300. The inlet volume 110 can be defined by any suitable geometric structure for liquid flow, for example a cylindrical tube or pipe 112 with centerline 112A as illustrated in FIGS. 1-5. The first fluid outlet 124 likewise can be an outlet to the bioreactor 200 as well as the insert apparatus 100, such that effluent (e.g., remediated wastewater permeate or otherwise) leaving the insert apparatus 100 via the first fluid outlet 124 also exits the bioreactor 200 without recontacting the bioreactor reaction medium 300. The outlet volume 120 can be defined by any suitable geometric structure for liquid flow, for example an annular tube or pipe 122 with centerline 112A as illustrated in FIGS. 1-4 or as a cylindrical tube or pipe 122 with centerline 122A as illustrated in FIG. 5.

The insert apparatus 100 further includes a plurality of exit volumes 130 and a plurality of recirculation volumes 140. Each exit volume 130 can be in direct or indirect fluid communication with the inlet volume 110, and it includes at least one exit biofilm support 134 positioned at a boundary between the exit volume 130 and an external volume 150 outside the bioreactor insert apparatus 100 (e.g., and suitably within the bioreactor 200 and/or reaction medium 300 therein). The external volume 150 generally includes the area outside of the apparatus 100, in particular the area external to the volumes 110, 120, 130, and 140. The exit biofilm support 134 is adapted to promote growth, attachment, and metabolism of microorganisms in the form of a biofilm 136 thereon. The exit biofilm support 134 is adapted to permit fluid and solid transport across the support 134 as well as between the exit volume 130 and the external volume 150, for example based on its partially open structure as defined by a mesh or other suitable structure. When the exit biofilm support 134 further includes the biofilm 136 thereon, fluid (liquid and gas) transport between the volumes 130/150 is still permitted, but solid transport could be still permitted, somewhat impeded, or substantially prevented, depending on the nature of the biofilm 136 and its attachment to the support 134. A relatively thin and/or loosely attached biofilm 136 does not substantially limit solid transport, while a relatively dense and/or strongly attached biofilm 136 can at least partially limit solid transport. The exit volume 130 can be defined by any suitable geometric structure for liquid flow, for example a tube or pipe 132 connected directly to or otherwise in fluid communication with the inlet volume 110 as illustrated in FIGS. 1-5. Each recirculation volume 140 can be in direct or indirect fluid communication with the outlet volume 120, and it includes at least one recirculation biofilm support 144 positioned at a boundary between the recirculation volume 140 and the external volume 150 outside the insert apparatus 100. The recirculation biofilm support 144 is adapted to promote growth, attachment, and metabolism of microorganisms in the form of a biofilm 146 thereon. The recirculation biofilm support 144 is adapted to permit fluid and solid transport across the support 144 as well as between the recirculation volume 140 and the external volume 150, for example based on its partially open structure as defined by a mesh or other suitable structure. When the recirculation biofilm support 144 further includes the biofilm 146 thereon, fluid (liquid and gas) transport between the volumes 140/150 is still permitted, but solid transport could be still permitted, somewhat impeded, or substantially prevented, depending on the nature of the biofilm 146 and its attachment to the support 144 as described above for the support 134/biofilm 136. The recirculation volume 140 can be defined by any suitable geometric structure for liquid flow, for example a tube or pipe 142 connected directly to or otherwise in fluid communication with the outlet volume 110 as illustrated in FIGS. 1-5. The microorganisms or microbes forming the biofilms 136, 146 are not particularly limited and can include bacteria (e.g., anaerobic, anoxic, or aerobic), archaea, or other microorganisms such as algae or other eukarya as well as viruses. Any microbial community that forms a biofilm is suitable.

Although the bioreactor insert apparatus 100 is generally illustrated in the figures as a tree-type structure with central flow conduits (e.g., inlet and outlet volumes 110, 120) and a plurality of outwardly directed biofilm support and flow conduits attached thereto (e.g., exit and recirculation volumes 130, 140), the insert apparatus 100 is not limited to the particularly illustrated structure. The insert apparatus 100 is generally designed to provide a relatively high total surface area (A) of all biofilm supports 134, 144 combined (e.g., on all exit volumes 130 and recirculation volumes 140), relevant because the surface area is the corresponding area for biofilm 136, 146 formation and microorganism metabolism to which the overall reaction rate is proportional. The relative surface area of the insert apparatus 100 can be expressed in a variety of ways. For example, a relative surface area ratio ($A/V_A$) can be defined as the total surface area (A) described above relative to the bioreactor insert apparatus 100 volume ($V_A$), for example including the total volume from the inlet volume 110 (e.g., cylinder), the outlet volume 120 (e.g., annulus), the exit volumes 130 (e.g., exit tubes), and the recirculation volumes 140 (e.g., recirculation tubes). In some embodiments, the ratio ($A/V_A$) can be at least 1 m$^{-1}$ (or equivalently 1 m$^2$/m$^3$ as a specific surface area parameter). There is no particular upper bound, as it can be desirable to maximize or otherwise increase the ratio ($A/V_A$) with any desired geometry and/or manufacturing technique (e.g., a 3D printing process as illustrated in the examples or otherwise). Taking into account other operational characteristics of the insert apparatus 100 (e.g., pressure drop during operation), the ratio ($A/V_A$) suitably can be in a range from 1 m$^{-1}$ to 1000 m$^{-1}$, for example at least 1, 2, 3, 5, 10, 20, or 50 m$^{-1}$ and/or up to 5, 10, 15, 20, 50, 100, 200, 500, or 1000 m$^{-1}$. Alternatively or additionally, a relative surface area ratio ($AN_R$) can be defined as the total surface area (A) described above relative to the bioreactor 200 volume ($V_R$), for example including the volume of the bioreactor 200 reaction vessel 210 or the interior reaction volume 220/reaction medium 300 volume. In some embodiments, the ratio ($AN_R$) can be at least 0.1 m$^{-1}$ (or equivalently 0.1 m$^2$/m$^3$ as a specific surface area parameter). As noted above, there is no particular upper bound, as it can be desirable to maximize or otherwise increase the ratio (ANR). Taking into account other operational characteristics of the insert apparatus 100 (e.g., pressure drop during operation), the ratio ($AN_R$) suitably can be in a range from 0.1 m$^{-1}$ to 100 m$^{-1}$, for example at least 0.1, 0.2, 0.3, 0.5, 1, 2, or 5 m$^{-1}$ and/or up to 0.5, 1, 1.5, 2, 5, 10, 20, 50, or 100 m$^{-1}$.

Figure 13:
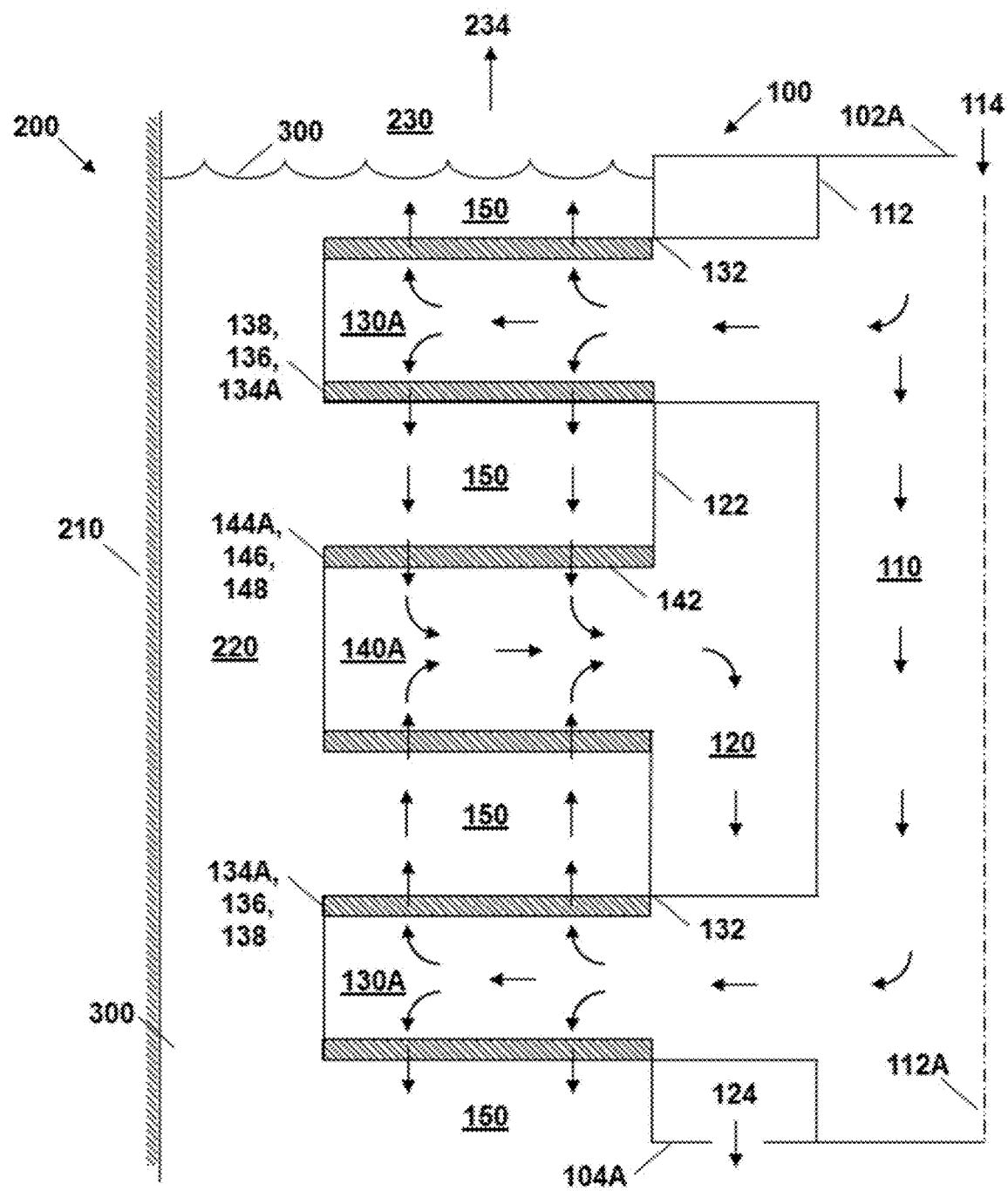
FIG. 13 illustrates a bioreactor insert apparatus with modular components and a corresponding bioreactor according to the disclosure.

In an embodiment and as noted above, bioreactor insert apparatus 100 can be formed by a 3D printing or additive manufacturing process. For example, a 3D printing or additive manufacturing process can be used to form the entire insert apparatus 100 or one or more components thereof, such as the inlet and/or outlet structures, 102, 104, the exit and/or recirculation volumes 130, 140, the biofilm supports 134, 144, etc. The specific types of materials used in the 3D printing process and the corresponding insert apparatus 100 structure are not particularly limited, for example including any suitable metal, plastic, or ceramic material amenable to an additive manufacturing process. Example materials include stainless steels, polypropylenes (PP), nylons/polyamides (PA), acrylic resins, and polyethylene terephthalates (PET). The use of 3D printing to form the insert apparatus 100 can provide advantages such as selection of a custom geometric design to improve or control operation of the insert apparatus 100 and corresponding bioreactor 200. The use of 3D printing can also provide modular designs for the insert apparatus 100 such that certain components thereof can be changed or replaced while other components can continue to be used in their current form. Such modular design can allow selective replacement of damaged or worn components, and it can also allow selective replacement of components with different materials or geometries for different operational characteristics of the insert apparatus 100 and bioreactor 200. FIG. 13 illustrates a bioreactor insert apparatus 100 with one or more modular components, such as one or more of a modular inlet 102A, a modular outlet 104A, a modular exit volume 130A, a modular recirculation volume 140A, and modular biofilm supports 134A, 144A.

Figure 3:
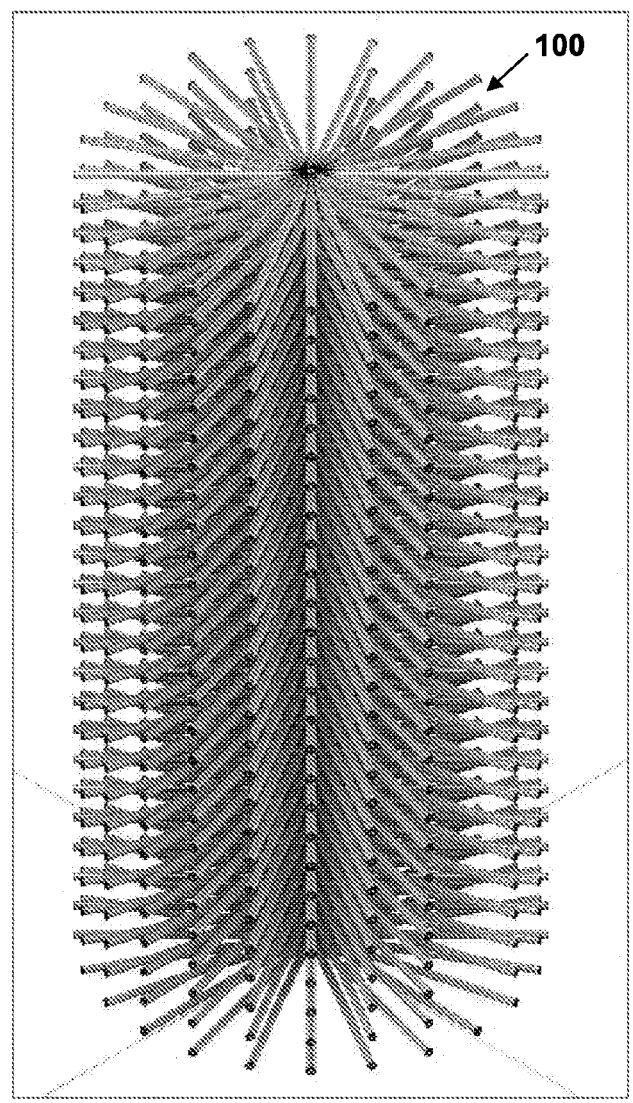
FIG. 3 is a cut-away side view of a bioreactor insert apparatus according to the disclosure.
Figure 4:
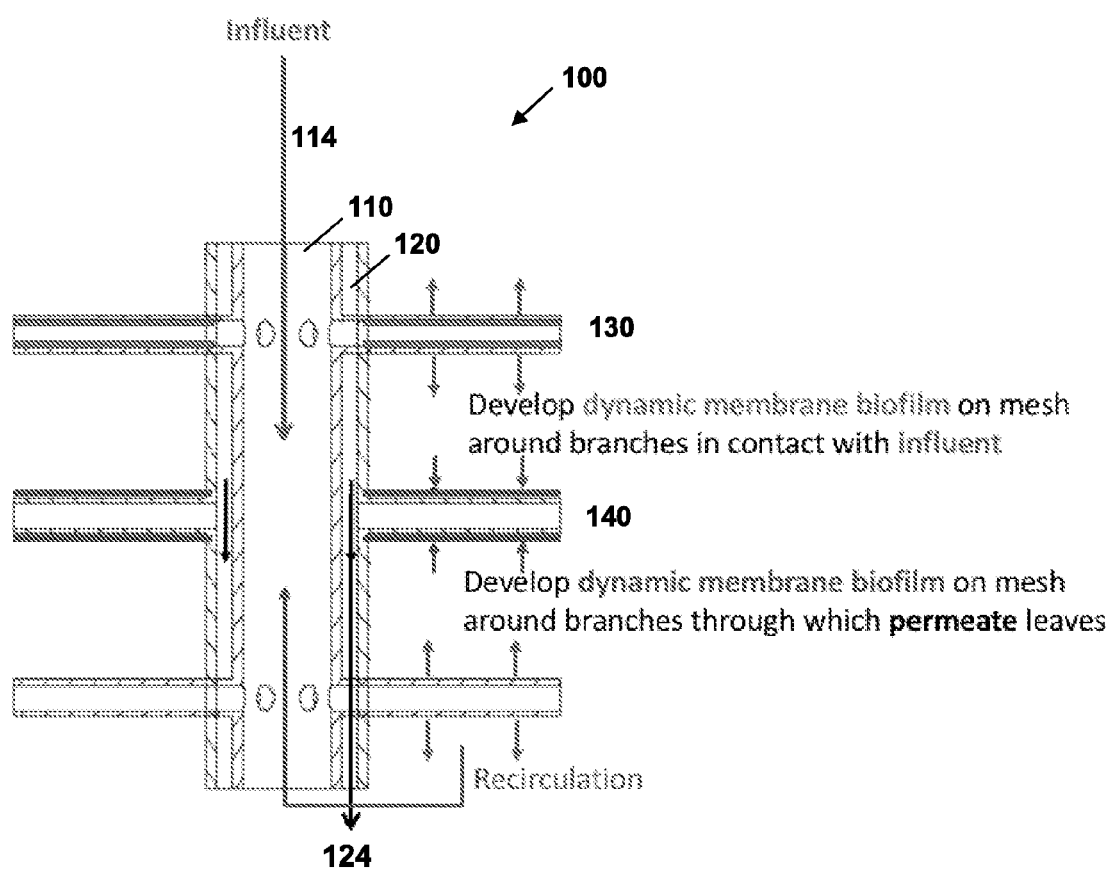
FIG. 4 is a perspective view of a bioreactor insert apparatus according to the disclosure and illustrating an increased specific surface area for biofilm supports/biofilms.

In an embodiment and as generally illustrated in FIGS. 1-4, the bioreactor insert apparatus 100 can be a single (unitary) structure, for example where a single insert apparatus 100 or multiple insert apparatus 100 can be placed within the bioreactor 200 for operation. The single-structure apparatus 100 can include the inlet volume 110, the outlet volume 120 attached or mounted to/around the inlet volume 110 (e.g., as an annular region as illustrated), the plurality of exit volumes 130 attached or mounted to/around the inlet volume 110 and in fluid communication therewith (e.g., as tubes as illustrated), and the plurality of recirculation volumes 140 attached or mounted to/around the outlet volume 120 and in fluid communication therewith (e.g., as tubes as illustrated). In the particular illustrated embodiment, the inlet volume 110 can include a cylindrical tube 112 in fluid communication with the first fluid inlet 114. The cylindrical tube 112 defines a central axis 112A generally corresponding to the centerline of the cylindrical tube 112. The outlet volume 120 can include an annular tube 122 around the cylindrical tube 112 and in fluid communication with the first fluid outlet 124 (e.g., with the annular tube 122 generally having the same central axis/centerline 112A as the cylindrical tube 112). The exit volumes 130 can include (cylindrical) exit tubes 132 in fluid communication with the cylindrical tube 112 inlet volume 110, for example being mounted to and extending radially outward relative to the central axis 112A of the cylindrical tube 112. The recirculation volumes 140 can include (cylindrical) recirculation tubes 142 in fluid communication with the annular tube 122 outlet volume 120, for example being mounted to the annular tube 122 and extending radially outward relative to the central axis 112A. Although the tubes 132, 142 are illustrated as cylindrical tubes, they can have any desired shape (e.g., tube or duct with a square, rectangular, or other cross section) with the general function of increasing the available biofilm 136, 146 surface area (A) and/or the relative ratios $(A/V_A)$ and $(A/V_R)$. In representative embodiments, suitable L/D ratios for the tubes 132, 142 can range from 2 to 100 (e.g., at least 2 and/or up to 100). FIG. 3 illustrates an embodiment with relatively long, thin tubes 132, 142 (i.e., relatively higher L/D ratios) for comparatively more relative surface area, for example in relation to the embodiments in FIGS. 2 and 4.

In an embodiment and as generally illustrated in FIG. 5, the bioreactor insert apparatus 100 can include two separate structures, including a first (or inlet/influent/feed) structure 102 and a second (or outlet/effluent/permeate) structure 104. The first structure 102 includes the inlet volume 110 and the exit volumes 130 mounted thereto. The second structure 104 includes the outlet volume 120 and the recirculation volumes 140 mounted thereto. The first and second structures 102, 104 are separate structures with the exit volumes 130 being in fluid communication with the recirculation volumes 140 via the external volume 150, reaction interior volume 220, and/or reaction medium 300. In this embodiment, a single first structure 102 or multiple first structures 102 as well as a single second structure 104 or multiple second structures 104 can be placed within the same bioreactor 200 for operation (e.g., with the same or different number of first and second structures 102, 104 in the bioreactor). In an alternative of this embodiment (not shown), at least one first structure 102 can be placed within a first bioreactor and at least one second structure 104 can be placed within a second bioreactor for operation, for example when the reaction medium from the first reactor is in fluid communication with the reaction medium from the second reactor, in which case reaction medium passing through the first structure 102 and into the first reactor reaction medium can then travel to the second reactor reaction medium and into/through the second structure. The first structure 102 can include the inlet volume 110 and the plurality of exit volumes 130 attached or mounted to/around the inlet volume 110 and in fluid communication therewith (e.g., as tubes as illustrated). The second structure 104 can include the outlet volume 120 and the plurality of recirculation volumes 140 attached or mounted to/around the outlet volume 120 and in fluid communication therewith (e.g., as tubes as illustrated). In the particular illustrated embodiment, the inlet volume 110 can include a cylindrical tube 112 in fluid communication with the first fluid inlet 114. The cylindrical tube 112 defines a central axis 112A generally corresponding to the centerline of the cylindrical tube 112. Likewise, the outlet volume 120 can include a cylindrical tube 122 in fluid communication with the first fluid outlet 124. The cylindrical tube 122 defines a central axis 122A generally corresponding to the centerline of the cylindrical tube 122. The exit volumes 130 can include (cylindrical) exit tubes 132 in fluid communication with the cylindrical tube 112 inlet volume 110, for example being mounted to and extending radially outward relative to the central axis 112A of the cylindrical tube 112. The recirculation volumes 140 can include (cylindrical) recirculation tubes 142 in fluid communication with the cylindrical tube 122 outlet volume 120, for example being mounted to and extending radially outward relative to the central axis 122A of the cylindrical tube 122.

In some embodiments, the first fluid outlet 124 can be in fluid communication with the first fluid inlet 114, for example including piping/tubing connections external to the bioreactor insert apparatus 100 and/or to the bioreactor 200 system more generally. In this way, the apparatus 100 and/or bioreactor 200 can include an external recycle of effluent 124A that has gone through one pass of the insert apparatus 100 such that a portion of the effluent can be recycled for further passes in the insert apparatus 100 if desired, thus being mixed with feed prior to being introduced via the first fluid inlet 114. Likewise, a portion of the effluent can be withdrawn as a final product stream 402 or 406, for example being passed through an external membrane filter 400 for final clarification.

The bioreactor insert apparatus 100 includes a plurality of exit volumes 130 and a plurality of recirculation volumes 140, the specific number of which is not particularly limited, and can be the same or different as between the exit volumes 130 and the recirculation volumes 140. For example, the number of exit volumes 130 can be at least 10, 20, 30, 40, 50, 60, 80, 100, 150, or 200 and/or up to 20, 40, 60, 80, 100, 120, 160, 200, 300, 400, 500, or 1000. The foregoing ranges generally correspond to the number of exit volumes 130 for a single apparatus 100 or a single inlet volume 110 (e.g., cylindrical tube 112 as illustrated). Generally, a larger number of exit volumes 130 increases the biofilm support 134/biofilm 136 surface area (A) relative to the volume of the apparatus 100 $(V_A)$, thus also increasing the specific biological activity of the apparatus 100 but also potentially increasing the pressure drop across the apparatus 100. The number of recirculation volumes 140 can be generally in the same ranges as for the exit volumes 130. In various embodiments, there can be more or fewer recirculation volumes 140 as compared to exit volumes 130. For example, the number of recirculation volumes 140 relative to the number of exit volumes 130 can be at least 0.2, 0.4, 0.6, 0.8, 0.9, or 1.0 and/or up to 1, 1.2, 1.5, 2, 3, 4, or 5. Generally, a larger number of recirculation volumes 140 increases the biofilm support 144/biofilm 146 surface area (A) relative to the volume of the apparatus ($V_A$), thus increasing the specific biological activity of the apparatus 100 but also potentially increasing the pressure drop across the apparatus 100.

In an embodiment, the biofilm supports 134 and/or 144 can be in the form of a mesh, for example a grid structure with substantial open areas between grid wires or elements. The biofilm supports 134 and/or 144 more generally can be any solid support structure, preferably one with periodic or otherwise distributed holes or orifices therein to promote liquid-biofilm contact and flow between exit volumes 130, recirculation volumes 140, and the external volume 150 of liquid and solids, such as suspended anaerobic, anoxic, and/or aerobic microorganisms and/or suspended solids from a wastewater influent feed to the apparatus 100 and/or the bioreactor 200. The biofilm supports 134, 144 provide some flow resistance, in particular when biofilms 136, 146 are on the supports 134, 144. The flow resistance limits (but does not prevent) mixing between adjacent compartments, which in turn allows metabolic activity by microorganisms in the biofilm 136 as inlet fluid passes from the inlet volume 110, into an individual exit volume 130, through the biofilm support 134 with biofilm 136 thereon, and into the external volume 150 corresponding to the bulk reaction medium 300. Depending on the coarseness/fineness of the biofilm support 134 and the density/thickness of the biofilm 136 thereon, some, all, or none of the particulate solid material in the inlet feed can be retained by or transmitted through the biofilm support 134/biofilm 136 from the exit volume 130 to the external volume 150. Likewise, there can be metabolic activity by microorganisms in the biofilm 146 as fluid passes from the bulk reaction medium 300, through the biofilm support 144 with biofilm 146 thereon, into an individual recirculation volume 140, and into the outlet volume 120. Similarly, depending on the coarseness/fineness of the biofilm support 144 and the density/thickness of the biofilm 146 thereon, some, all, or none of the particulate solid material in the bulk reaction medium 300 can be retained by or transmitted through the biofilm support 144/biofilm 146 from the external volume 150 to the recirculation volume 140. The biofilms 136, 146 generally transmit and/or generate influent organic (reactant) species, intermediate metabolic products (e.g., organic acids), and final metabolic products (e.g., methane). The biofilm supports 134, 144 as a mesh or other structure with open areas can have mesh spacings/open areas on the micron scale, for example on the order of $10^0$ microns, $10^1$ microns, or $10^2$ microns. Standard mesh designations such as 20 mesh (841 microns) to 400 mesh (37 microns) can be used, as well as smaller or other non-standard mesh sizes. More generally, suitable mesh spacings/open areas can be in a range from 1 micron to 1000 microns, for example at least 1, 2, 5, 10, 20, 50, 100, or 200 microns and/or up to 10, 20, 50, 100, 200, 500, 700, 900, or 1000 microns.

In an embodiment, the biofilm supports 134 and/or 144 can include an electrically conductive material, for example being formed from a metallic material, a conductive carbon material, or otherwise electrically conductive material, such as a metallic mesh or a high-surface area conductive carbon mesh. The electrically conductive biofilm supports 134, 144 permit electron transport within the supports 134, 144, but the supports 134, 144 are not necessarily connected to an external electrical power supply or voltage source, for example being electrically insulated relative to the reaction vessel (wall) and other biofilm supports. The electrically conductive biofilm supports 134, 144 allow transport of electrons between biofilm microorganisms thereon, some of which can generate electrons during metabolic (oxidation) processes, and some of which can consume electrons during metabolic (reduction) processes, thereby promoting syntrophic metabolic pathways between biofilm microorganisms. In a further embodiment, the biofilm supports 134, 144 can include an electrically conductive carbon cloth mesh (e.g., activated carbon cloth mesh with high specific surface area), for example on a stainless steel or other metallic/electrically conductive support structure.

In an alternative embodiment, the biofilm supports 134 and/or 144 can include an electrically resistive material, for example being formed from an electrically resistive or insulating material such as various plastic materials, natural or synthetic rubbers, or silicon/silicon-based materials. One or more components of the insert apparatus 100 similarly can include an electrically resistive material, for example the inlet, outlet, exit, and/or recirculation volumes 110, 120, 130, 140. Examples of suitable electrically resistive or insulating plastic materials include polyethylene terephthalates (PET), polybutylene terephthalates (PBT), polyether sulfones (PES), polyether ether ketones (PEEK), polypropylenes (PP), polyvinyl chlorides (PVC), etc. The specific resistance or electrical resistivity of the electrically resistive or insulating materials is not particularly limited, but it is suitably at least about $10^{-6}$, $10^0$, $10^2$, $10^6$ or $10^{10}$ ohm·m and/or up to about $10^2$, $10^{10}$, $10^{16}$ or $10^{26}$ ohm·m. The electrically resistive material is adapted to heat under electrical current, for example as applied by an external source or other means. For example, an external power source can be electrically connected to the biofilm supports 134, 144, and/or other insert apparatus 100 component (e.g., in single or separate electrical circuits) to produce an electrical current through the supports, which current in turn induces electrical resistance heating in the supports specifically and the reactor environment more generally (e.g., due to heat convection and conduction away from the supports). In some embodiments, the source of current in the supports can be one or more solar panels in electrical connection with the supports, or the source of current can be derived from microorganisms growing in the reactor (e.g., with such microorganisms as could be used in a microbial fuel cell). The heating effect from the electrically resistive supports can be such that the bioreactor can be operated at a mesophilic temperature (e.g., 20° C. to 40° C. or 30° C. to 40° C.) or at a thermophilic temperature (e.g., 40° C. to 60° C.), for example with or without another heating source such as a heating jacket for the reactor, etc.

In an embodiment, the bioreactor 200 can further include attachment or carrier media for microbial growth, for example in the interior reaction volume 220. During operation of the insert apparatus 100 and/or corresponding bioreactor 200, the attachment media can be suspended or otherwise dispersed and circulating in the corresponding aqueous reaction medium 300. The attachment media provide additional surface area within the bioreactor 200 to promote the growth, attachment, and metabolism of microorganisms thereon at locations other than the biofilm supports. The materials for the attachment media are not particularly limited, but they suitably include plastics or polymers, carbon materials, and/or cellulosic materials in particulate form. Suitable materials include plastics such as polyethylenes (PE), high density polyethylenes (HDPE), or polypropylenes (PP), carbon materials such as activated carbon or carbon fibers, and cellulosic materials such as wood chips or fibers. In some embodiments, one or more components or surfaces of the bioreactor 200 and/or apparatus 100 can be formed from similar materials to also promote microorganism growth thereon. The attachment media can have any suitable geometric shape and/or size, for example a geometry that provides sufficient (specific) surface area for microorganism growth and that allows the attachment media to be maintained in suspension during operation of the bioreactor 200. More specifically, the attachment media can be selected so that circulating fluid motion within the bioreactor 200 maintains the attachment media in suspension in the aqueous reaction medium 300 without substantial separation or segregation of the attachment media (e.g., via settling or flotation, depending on the density of the attachment media), For example, the attachment media in particulate form can have a diameter or size in a range from 0.1 µm to 1000 µm, for example at least 0.1, 0.2, 0.5, 1, 2, 5, 10, 20, or 100 µm and/or up to 0.5, 1, 2, 5, 10, 20, 50, 100, 200, or 1000 µm, whether as a size range or average size (e.g., number-, weight-, area-, or volume-based range or average). Alternatively or additionally, the attachment media can have a specific surface area in a range from $1 \text{ m}^{-1}$ to $10,000 \text{ m}^{-1}$ (i.e., $\text{m}^2/\text{m}^3$) for example at least 1, 2, 5, 10, 20, 50, or $100 \text{ m}^{-1}$ and/or up to 10, 20, 50, 100, 200, 500, 1000, 5000, or $10000 \text{ m}^{-1}$, whether as a range or average specific surface area.

During operation of the insert apparatus 100 and/or corresponding bioreactor 200, the apparatus 100 further includes the biofilms 136, 146 adhered to their respective biofilm supports 134, 144, for example including a biofilm on all exit and recirculation supports 134, 144. Biofilms generally include a group of microorganisms in which distinct cells stick to one another and adhere to a surface. The adherent cells become embedded in a slimy extracellular matrix polymeric substance as a type of hydrogel. Biofilms are useful in industrial settings where beneficial bacterial biofilms can use organic pollutants as an energy source. Digestion of these compounds removes them from a waste stream and releases environmentally benign substances and/or substances useful as reaction product (e.g., methane). The community of microorganisms or microbes forming the biofilms 136, 146 are not particularly limited and can include bacteria (e.g., anaerobic, anoxic, or aerobic), archaea, or other microorganisms such as algae (e.g., for biofuel component production) or other eukarya as well as viruses. Any microbial community that forms a biofilm is suitable. In some embodiments, the biofilm populations can include microbial species collectively having biological activity, for example methanogenic activity. In some embodiments, at least some microorganisms in the biofilms (and reactor) are methanogens, producing methane from one or more components (e.g., organic or other components) in the influent feed and/or as produced by other microorganisms as intermediates such as organic acid intermediates (e.g., volatile organic acids or otherwise). The microorganisms in the biofilm can be selected to have a specific population distribution of different species to provide a desired/tuned composition for digesting waste streams from distinct sources and having a distinct profile of contaminants. The bioreactor 200 can further include suspended microorganisms in the reaction medium 300, which microorganisms can be the same, similar, or different populations of microorganisms (e.g., bacteria, archaea) as in the biofilm with same, similar, or different activities, for example with a different distribution of species types between the free, suspended microorganisms and the adhered, biofilm microorganisms. Likewise, the exit biofilms 136 can have the same, similar, or different community of microorganisms with the same, similar, or different activities as compared to the recirculation biofilms 146. In this way, the biofilms 136, 146 can have the same or different functions, for example with respect to biological activity (e.g., amount or type of products formed) and/or resistance to solids transport.

While the insert apparatus 100 and corresponding bioreactor 200 are particularly illustrated and described in the context of wastewater treatment reactors for methane generation, the apparatus 100 and bioreactor 200 can be used in any context in which the biofilms have corresponding biological activity to convert one or more reaction system reactants or intermediates to one or more desired biological intermediates or products therefrom. Representative examples broadly include fermentation, biopharmaceutical production, assembly of biomolecules, etc. Industrial or other large-scale fermentation is a particularly suitable application for the insert apparatus 100, in particular for open fermentation applications which utilize mixed microbial communities. In various fermentation processes, singular or groups of microorganisms are used in fermenters or bioreactors to produce a desired product. In such applications, the insert apparatus 100 can be used as a bioreactor component for increasing substrate/microorganism contact and organizing microbial communities on its meshes or supports, thereby improving product yields. Examples of suitable types of fermenters or bioreactors include continuously stirred tank reactors (CSTRs), membrane bioreactors (MBRs, such as for ethanol and organic acid fermentation), microcarrier bioreactors, and fluidized bed bioreactors. Examples of suitable fermentation products include those with medical uses (e.g., thienamycin or other antibiotics), industrial or commodity chemicals (e.g., succinic acid or other organic acids; ethanol, propanol, butanol or other alcohols), alcoholic beverages (e.g., ethanol as a product itself or a component of a beer, liquor, or wine beverage), and food and feed products (e.g., glucoamylase or other digestive enzymes). In each of the foregoing fermentation settings, suitable singular or groups of microorganisms are generally known in the art and may be grown/deposited on the supports 134, 144 to form corresponding biofilms 136, 146.

In an embodiment, the insert apparatus 100 can further include a biofilm seed 138, 148 or precursor adhered to the biofilm supports 134 and/or 144, respectively. For example the biofilm seed 138, 148 can be on some or all exit supports 134 and recirculation supports 144, which can be the same or different seed for the different supports. The biofilm seed 138, 148 can be provided already on the supports 134, 144 prior to operation of the corresponding bioreactor 200 so that start-up times required to establish a newly operational insert apparatus 100 and bioreactor 200 and with a desired biofilm population are reduced. For example, the supports 134, 144 can be inoculated or otherwise coated with a population of (live or dormant) microorganisms, and then the microorganisms can be coated, covered, or otherwise adhered to the supports 134, 144. Suitable coatings include water-soluble binders or adhesives (e.g., a water-soluble polymer such as a water-soluble epoxy or polyvinyl alcohol) applied as a matrix (e.g., an air-tight matrix) on the supports 134, 144 to hold the microorganisms in place in the matrix until startup of the insert apparatus 100 and bioreactor 200. The microorganisms are suitably dormant while fixed in the matrix in their seed or precursor form (e.g., as a result of not being fed with substrate while therein). When the insert apparatus 100 is flooded with water, for example an aqueous reactor feed (e.g., wastewater or otherwise) and/or an aqueous microorganism nutrient medium, the water-soluble matrix is removed, exposing and activating the supported microorganisms, thus allowing them to grow and attach to the supports 134, 144 as corresponding biofilms 136, 146. This activation and startup process can be prior to or concurrent with use of the insert apparatus 100 and bioreactor 200 in normal production with circulation through the apparatus.

The bioreactor 200 generally includes a reaction vessel 210 defining an interior reaction volume 220 therein. The reaction vessel 210 can be open or closed to the external environment, but suitably is closed when a gaseous reaction bioproduct (e.g., methane) is recovered from the bioreactor 200. The reaction volume 220 is generally the location where the reaction medium 300 (e.g., aqueous reaction medium with reactants, products, and/or suspended microorganisms) is present during operation of the bioreactor 200. The bioreactor 200 can further include a headspace portion 230 of the reaction vessel 210 and a bioreactor gas outlet 234 in fluid communication with the headspace portion 230. The headspace portion 230 is generally the upper portion of the reaction vessel 230, which portion is not occupied by liquid reaction medium 300 during bioreactor 200 operation and contains metabolic product gas(es) produced by the biofilms 136, 146 and/or in the liquid reaction medium 300 (e.g., via suspended microorganisms). The metabolic product gas(es) so produced have sufficient residence time within the bioreactor 200 to enter the gas phase in the headspace 230 (e.g., attaining equilibrium or near equilibrium). In particular, relatively higher production of methane or other gas products at the biofilm surface combined with recirculation within the bioreactor 200 provides time for gas product equilibration in the liquid phase (i.e., where methane or other gas products can be originally produced at above-equilibrium concentrations in the biofilm and neighboring reaction medium) and release/capture of gaseous products in the headspace 230. This increases methane or other gas product yield/recovery and reduces (undesirable) gas product loss in the bioreactor 200 effluent, which can represent both a loss of desired product and a potential environmental pollutant (e.g., in the case of methane as a greenhouse gas). The gas outlet 234 is for removal and recovery of any metabolic gas products produced in the bioreactor 200, for example including methane or other gas products.

In an embodiment, the bioreactor insert apparatus 100 can be rotatably mounted within the reaction vessel 210. During operation of the bioreactor 200, rotation of the bioreactor insert apparatus 100 can help to create a well-mixed bulk reactor medium 300 external to the rotating apparatus 100 and within the reaction vessel 200. In this case, an axisymmetric geometric design for the apparatus 100 as generally illustrated in FIGS. 1-5 provides an additional benefit in that the radial mesh/biofilm arms 130, 140 provide not only an increased surface area for biological reaction, but also an impeller-type structure for bulk reactor medium 300 shearing at a rate that does not damage the microorganisms but which still provides mixing. Rotation of the apparatus 100 can be performed in a bioreactor 200 with a single or multiple apparatus 100 rotatably mounted therein, and/or with a single or multiple first/second structures 102, 104 rotatably mounted therein. For example, as illustrated in FIG. 5, overall bioreactor 200 feed enters into the inlet volume 110 of the first structure 102 and flows radially outward into the exit volumes 130, through meshes/biofilms 134, 136 thereon, and into the bulk reaction medium 300. Mixed fluid from the bulk reaction medium 300 then enters the recirculation volumes 140 on the second structure 104 in the bioreactor vessel 210, through meshes/biofilms 144, 146, into the outlet volume 120 of the second structure 104, and then out through the first fluid outlet 124 (e.g., for partial recycle and/or product withdrawal). The two structures 102, 104 (or multiple unitary apparatus 110 as in FIGS. 1-4) can be independently rotatable to provide mixing of the bulk reaction medium 300.

In an embodiment, the bioreactor 200 can further include a membrane filtration unit 400 in fluid communication with an outlet or effluent stream of the bioreactor 200, for example a non-recycled portion of the effluent from the first fluid outlet 124. In various embodiments, the membrane filtration unit 400 can include one or more of the following: a separation membrane, a membrane inlet 402 in fluid communication with the first fluid outlet 124 and a first (retentate) side of the separation membrane 400, a membrane retentate outlet 404 in fluid communication with the first fluid inlet 114 and the first (retentate) side of the separation membrane 400, and a membrane permeate outlet 406 in fluid communication with a second (permeate; opposing) side of the separation membrane 400 (e.g., as final, clarified effluent stream). The separation membrane can be a semi-permeable membrane adapted to retain solids and to selectively transmit or retain gases, liquids, and solutes therein based on size, solubility, ionic or non-ionic character, etc. as determined by membrane pore size, structure, chemical constituents, etc., as generally known in the art. The membrane generally retains bioreactor (microorganism) solids on the retentate side and transmits methane or other (dissolved) gaseous products, or other dissolved non-gaseous compounds, and water on the permeate side. The retentate can be recycled back to the bioreactor 200/bioreactor insert apparatus 100.

In another aspect, the disclosure relates to a method for forming a bioreactor product, for example including methane in a wastewater or other context, or other products altogether. An influent stream (e.g., wastewater influent) including one or more organic constituents or other reactants for biological conversion is fed to the bioreactor insert apparatus 100 via the first fluid inlet 114, such as with suitable pumping apparatus and/or suitable valves, piping, or other fitting structures. The bioreactor 200 first fluid inlet 114 further can receive and deliver into the bioreactor insert apparatus 100 a recycle stream of effluent from the first fluid outlet 124. Influent feed and recycle can be mixed together upstream of the first fluid inlet 114 and delivered into the apparatus 100 together, or they can be fed separately to the apparatus 100 at different fluid inlet locations. The influent stream is circulated through the inlet volume 110, into the exit volumes 130, through the exit biofilm supports 134 and biofilms 136 thereon, into the external volume 150 (e.g., into the reaction medium 300, through the recirculation biofilm supports 144 and biofilms 146 thereon), into the recirculation volumes 140, into the outlet volume 120, and through the first fluid outlet 124 (e.g., including suitable valves, piping, and/or other fitting structures). In FIG. 1, the arrows without reference numerals qualitatively indicate the direction of flow and circulation through the insert apparatus 100 and the bioreactor 200. During the circulation, one or more of the organic constituents or other reactants are converted to a product, both at the biofilm surfaces 136, 146 and in the aqueous reaction medium 300 bulk from suspended microorganisms therein. In an embodiment, the wastewater influent stream includes one or more organic constituents and other reactants for conversion (e.g., anaerobic, anoxic, or aerobic conversion), such as to methane or other product. Wastewater treatment refers to the process by which polluted water sources from domestic sources (sanitation) or industrial sources are converted into a clean effluent that can be returned to natural sources or used for other applications (e.g., irrigation). The disclosed bioreactor 200 and insert apparatus 100 can be used in wastewater treatment for the treatment of such contaminated water, for example while also producing a methane product. Wastewater influent streams can include a variety of organic constituents such as proteins, lipids, and/or carbohydrates. Examples of other wastewater components that serve as microorganism nutrients for metabolic conversion in the bioreactor 200 include ammonium ions (e.g., for aerobic conversion to nitrite and nitrate ions or salts), nitrate ions (e.g., for anoxic conversion to nitrogen gas), and phosphate ions (e.g., for conversion to polyphosphate for storage in microbes which are then collected).

In an embodiment, at least 50%, 65%, or 80% of total microorganisms in the bioreactor 200 are incorporated into the biofilms, for example as determined on a weight or number basis. Suitably, the remaining microorganisms are suspended in the bulk reaction medium 300 and/or within the insert apparatus 100, for example with the bulk reaction medium 300 and insert apparatus 100 having generally the same or similar concentrations of suspended microorganisms. Suitably at least 50, 65, 80, 85, 90, 95, or 98% and/or up to 90, 95, 97, 98, 99, or 100% of total microorganisms are incorporated into the biofilms 136, 146 with only a minor amount in the bulk reaction medium 300 and/or insert apparatus 100. Total biological activity in the bioreactor likewise can be at least 80, 85, 90, 95, or 98% and/or up to 90, 95, 97, 98, 99, or 100% attributed to biological activity/conversion at the biofilm 136, 146 surfaces. In some embodiments, the exit supports 134 buildup highly active biofilms 136 and are responsible for a majority of product formation (e.g., methane production in anaerobic configurations). In such cases, the biofilms 146 of the recirculating supports 144 are predominantly useful for solid/liquid separation, limiting solids in the reaction medium 300 from reentering the insert apparatus 100 via the recirculation volumes 140, although potentially still providing some biological activity.

In an embodiment, the biofilms 136, 146 have methanogenic activity. At least some microorganisms in the biofilm 136, 146 (and bioreactor 200) are methanogens, producing methane from one or more components in the influent feed and/or as produced by other microorganisms as intermediates such as organic acid intermediates. Suitably, aqueous fluid removed through the first fluid outlet 124 includes dissolved methane at a concentration in a range of 50% to 150% relative to the equilibrium concentration of methane in water, for example as determined by Henry's law (e.g., at the temperature and/or pressure conditions of the first fluid outlet 124). For example, the relative methane concentration can be at least 50, 70, 80, 90, 95, 99, or 100% and/or up to 110, 120, 135, or 150% relative to the equilibrium concentration of methane in water. The method can further include recovering a gas product stream including methane via the bioreactor gas outlet 234, for example containing about 60-95% methane, with the balance being substantially carbon dioxide and hydrogen.

In an embodiment, the method includes operating the bioreactor 200 at a temperature in a range of 1° C. to 60° C. In some cases, the bioreactor can be operated at a psychrophilic temperature such as 1° C. to 20° C., for example at least 1, 2, 3, 6, 8, 10, 12, or 15° C. and/or up to 5, 10, 15, or 20° C. In some cases, the bioreactor can be operated at a mesophilic temperature such as 20° C. to 40° C., for example at least 20, 25, or 30° C. and/or up to 30, 35, or 40° C. In some cases, the bioreactor can be operated at a thermophilic temperature such as 40° C. to 60° C., for example at least 40, 45, or 50° C. and/or up to 50, 55, or 60° C. The foregoing ranges are typical of wastewater treatment, for example representing the temperature of the reaction medium 300 and the fluid in the insert apparatus 100. More generally, any suitable temperatures can be used for other applications, whether for wastewater treatment or otherwise, in particular as long as such temperatures do not damage, kill, or otherwise inactivate the useful microorganisms in the biofilms. For example, reactor temperature can be used as a selection pressure to inactivate certain microbes, for example methanogen inactivation in a scenario where it is desired to select for spore-forming microbes that produce hydrogen as preferred product.

In an embodiment, the bioreactor can be operated over a relatively wide range of hydraulic retention time (HRT) values, in particular at relatively lower values that reflect its ability to operate at relatively high volumetric loading rates while still providing good microorganism activity. The HRT suitably can range from 2 hr to 40 hr, for example being at least 2, 5, 8, 10, 12, 15, or 20 hr and/or up to 10, 15, 20, 25, 30, or 40 hr. The HRT can be expressed as the ratio $V_R/Q$ reflecting the bioreactor 200 volume ($V_R$) relative to the inlet 114/114A volumetric flow rate (Q) to the bioreactor 200.

Examples

The following examples illustrate a bioreactor insert apparatus, corresponding bioreactor, and operation of the same according to the disclosure.

Sustainable water management is increasingly important for utilities and is driving efforts to reduce energy consumption and residuals production in water resource recovery facilities treating domestic wastewater without compromising effluent quality. Anaerobic membrane bioreactors (AnMBRs) are an appealing alternative to conventional aerobic domestic wastewater treatment systems because they do not require aeration energy, produce fewer residuals, have a smaller physical footprint, and produce biogas which can be used for energy generation. In fact, interest in AnMBRs has spurred extensive research, and many review papers have been published in recent years discussing process performance, membrane fouling, energy balance, and environmental impacts of both bench and pilot scale reactors. Studies have shown that AnMBRs can successfully treat a wide variety of wastewaters at mesophilic and thermophilic temperatures, and at psychrophilic temperatures in some applications. However, conclusions from review papers written several years ago are qualitatively the same as those published most recently: There remains a strong need for less energy-intensive fouling mitigation, higher membrane fluxes, handling of effluent dissolved methane, and treatment at ambient (often psychrophilic) temperatures in order to make AnMBRs advantageous to current treatment technology.

Harnessing biofilm activity is important for efficient treatment of low-strength wastewater under psychrophilic conditions at low hydraulic retention times (HRTs). Although biofilm activity is beneficial for organics removal, active biofilms on permeating membranes lead to methane production on the membrane surface, leading to higher dissolved methane concentrations than those predicted by equilibrium as determined by Henry's law. Dissolved methane (dCH4) is later released into the environment as a potent greenhouse gas, so high effluent dCH4 concentrations are undesirable for an AnMBR's environmental impact. Consequently, active biofilm development on non-permeating membrane surfaces could reduce dissolved methane concentrations to those governed by thermodynamic equilibrium. Low-energy fouling control and high membrane fluxes are necessary to make AnMBRs economically favorable to existing technology. The disclosed bioreactor insert apparatus utilizes dynamic membranes, those with larger membrane pore size than conventional microfiltration/ultrafiltration membranes. Anaerobic dynamic membrane bioreactors (AnDMBRs) reduce capital and operating costs due to their less expensive materials (e.g., nylon, silk, stainless steel) and because constant fouling mitigation (e.g., via biogas sparging) is not required.

A laboratory-scale bioreactor was formed using a 7 L glass vessel with a working (bulk) liquid volume of 5 L and a 3D-printed filtration structure as schematically represented by the bioreactor insert apparatus in FIGS. 1-4. Both the influent (or exit) branches or tubes and the permeating (or effluent/recirculation) branches or tubes were wrapped with 74 µm pore size stainless steel meshes. The total mesh area was 0.10 m$^2$ with 69% of the area on influent branches and 31% of the area on effluent branches. However, the openings on the branches that allow water to pass through make up only a portion of the mesh area for each branch, leading biofilms to develop on these regions. The bioreactor had a total permeating mesh area of 0.0164 m$^2$, which is 65% of the total mesh area through which water can pass from the insert apparatus interior to the bulk reactor volume and back into the insert apparatus.

During bioreactor operation, the transmembrane pressure (TMP) was measured and transmitted by an Ashcroft (Stratford, CT) SAE Compound Transmitter (30 to 0 to 30 In. Hg/psi) to an Arduino MEGA 2560 REV3 which logs the data onto an SD card in an Adafruit Assembled Data Logging Shield. Three peristaltic pumps (Cole-Palmer, IL) were used to pump in influent, recirculate mixed liquor, and extract permeate. The pumps were controlled by an Arduino controller, and a level sensor was used to control the feed rate to the reactor. Temperature and pH were recorded manually using a combined pH/temperature probe (Mettler Toledo, OH).

Synthetic wastewater (COD of 468±88 mg/L, alkalinity of 270 mg CaCO3/L, and pH of 6.5-7) was pulled into the reactor and combined from an acidified (pH 2.5-4.0), refrigerated concentrate and a basified (pH 8.5-9.0) dilution water tank. The combined synthetic influent flow could be sampled from a sample port downstream of the influent pump, prior to the influent entering the reactor. The wastewater was forced through a biofilm on the inside of the meshes on the influent branches. A pipe reaching the bottom of the reactor was used to recirculate mixed liquor back to the center of the 3D-printed structure and the wastewater was again forced through the biofilm on the influent branches. Recirculation samples could be collected from a port off of the recirculation tubing. Mixed liquor was forced through the biofilm on the permeating branches and could be sampled directly after the permeate pump. A TEDLAR polyvinyl fluoride gas bag (available from SKC Inc.) was used to collect the produced biogas.

The bioreactor was inoculated with anaerobic sludge from a pilot-scale AnMBR treating real domestic wastewater in Southeast Michigan (Northfield Wastewater Treatment Plant, Whitmore Lake, MI). A total biomass of approximately 41 g volatile suspended solids (VSS) was added to the current reactor, which would represent a mixed liquor volatile suspended solids (MLVSS) concentration of about 8200 mg/L. However, the recirculation pattern was designed so that most of the biomass should form on the meshes and not be suspended in this reactor. Total suspended solids concentrations in the reactor were about 40 mg/L, and estimated biomass washed out based on effluent suspended solids/turbidity was only around 11% of initial total biomass, indicating that most of the biomass had formed on the meshes. The reactor was operated at ambient conditions (about 23° C.) and an HRT of 15.5-16.5 hours, corresponding to an organic loading rate of 0.7-0.8 kg COD/m$^3$-day. No fouling mitigation was employed during operation. Infrequent backwashing with 20 mL of distilled water was used to clear clogs in the permeate line.

The reactor performance was assessed by monitoring influent, reactor, and effluent characteristics. These included chemical oxygen demand (COD; total and soluble), volatile fatty acids (VFAs), dissolved methane, and sulfate concentrations, suspended solids, and turbidity. Additionally, gas production and content and TMP were monitored. The following sections illustrate reactor performance over an approximate 50-day period after reactor startup.

Figure 6:
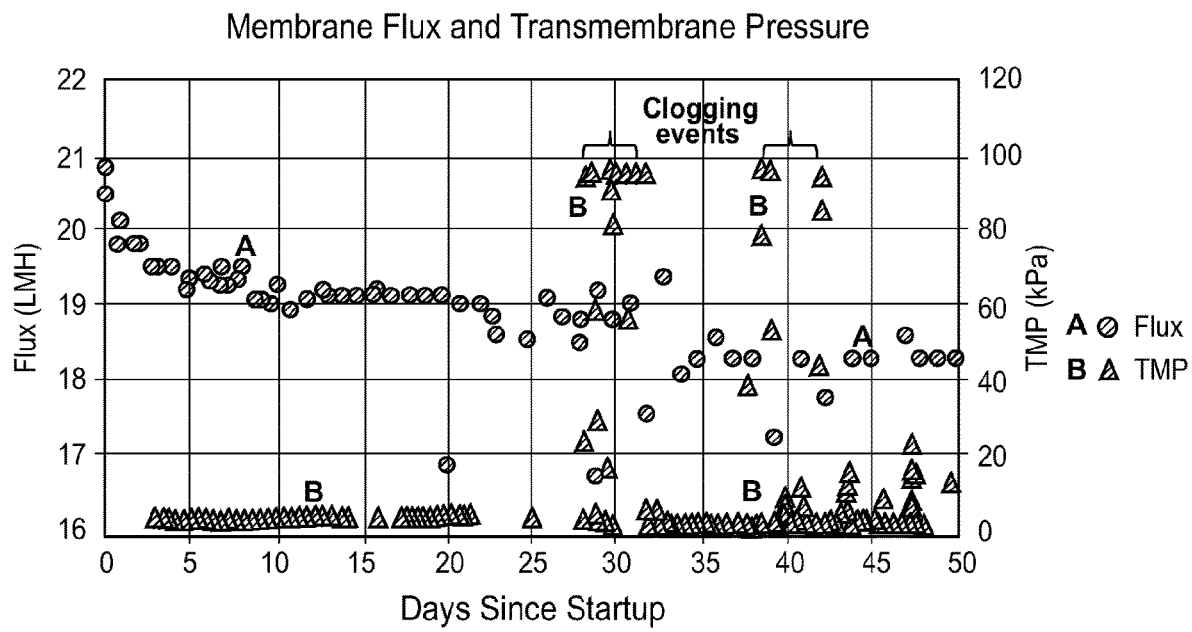
FIG. 6 is a graph illustrating membrane flux and transmembrane pressure as a function of time since startup for a bioreactor insert apparatus and corresponding bioreactor according to the disclosure.
Figure 7:
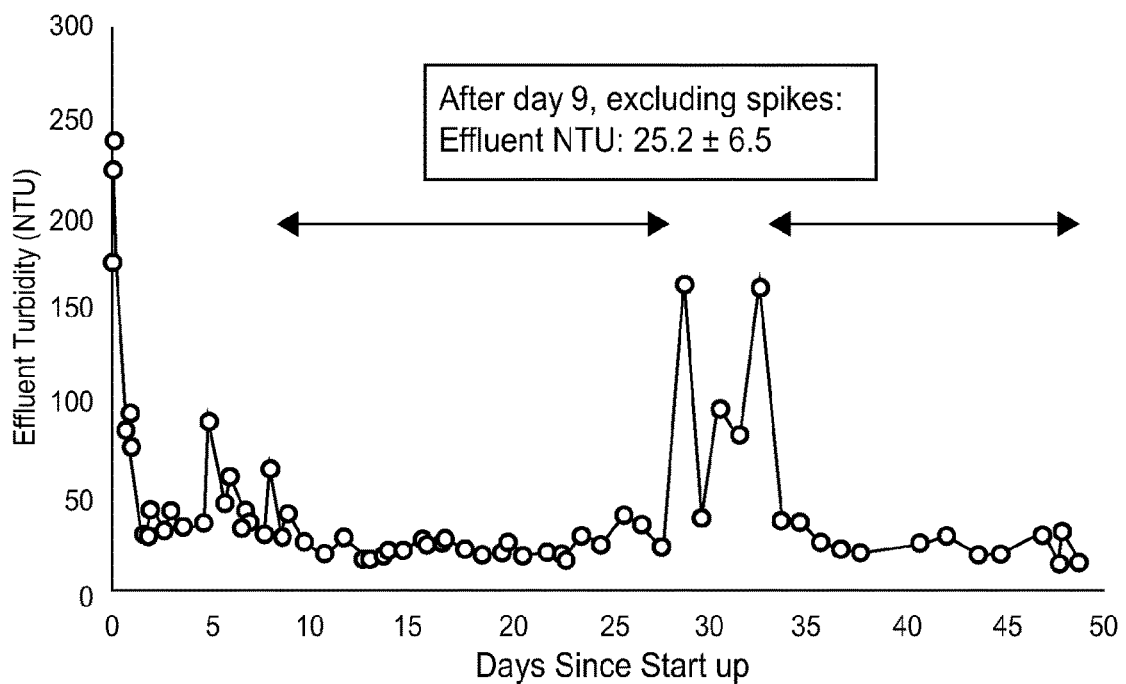
FIG. 7 is a graph illustrating effluent turbidity as a function of time since startup for a bioreactor insert apparatus and corresponding bioreactor according to the disclosure.

Dynamic Membrane Performance: Membrane (i.e., stainless steel mesh and associated biofilm) performance was evaluated by monitoring TMP, flux, and effluent turbidity. The TMP represents the difference in pressure between reactor headspace pressure, which was kept at atmospheric because it was always connected to a gas collection bag, and pressure in the permeate line. The flux was calculated by dividing the measured flow rate by the total permeating mesh area and reported in L/m$^2$-h (LMH). The TMP generally remained below 4 kPa, except during a few periods where a clog formed in the permeate tubing (FIG. 6), and generally remained in a range from 1-4 kPa (and generally below 2 kPa) after clogs were removed. The membrane flux was initially above 20 LMH and remained just above 18 LMH during operation (FIG. 6). The effluent turbidity, which indicates how well the dynamic layer is filtering solids (with lower turbidity corresponding to more filtering), fell from over 200 NTU to 30 NTU after an initial period of 9 days, and generally remained below 30 NTU afterwards, except after backwashing events, which disrupted the biofilm layer (FIG. 7).

Figure 8:
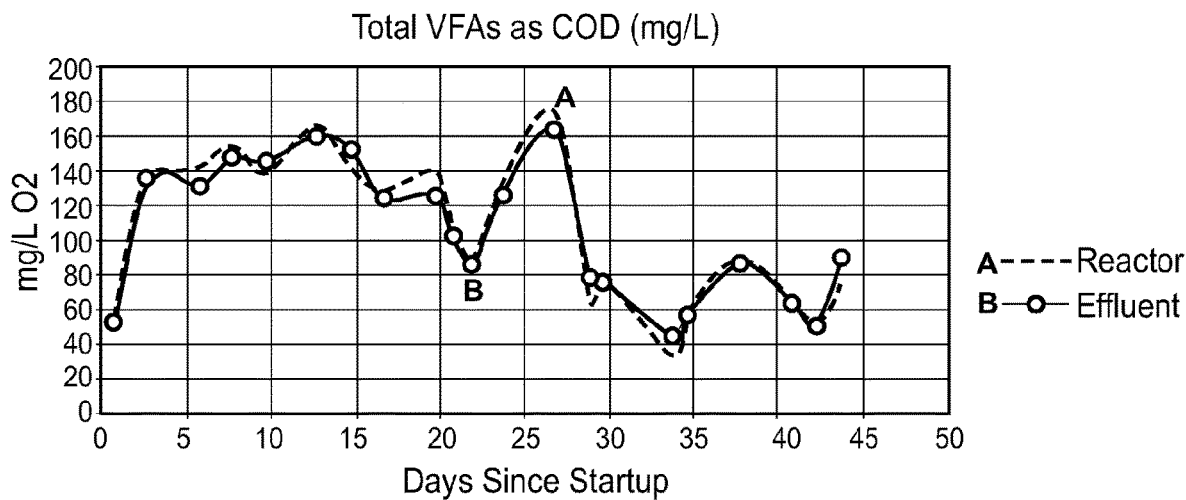
FIG. 8 is a graph illustrating total volatile fatty acids (VFAs) in the bioreactor and effluent as a function of time since startup for a bioreactor insert apparatus and corresponding bioreactor according to the disclosure.
Figure 9:
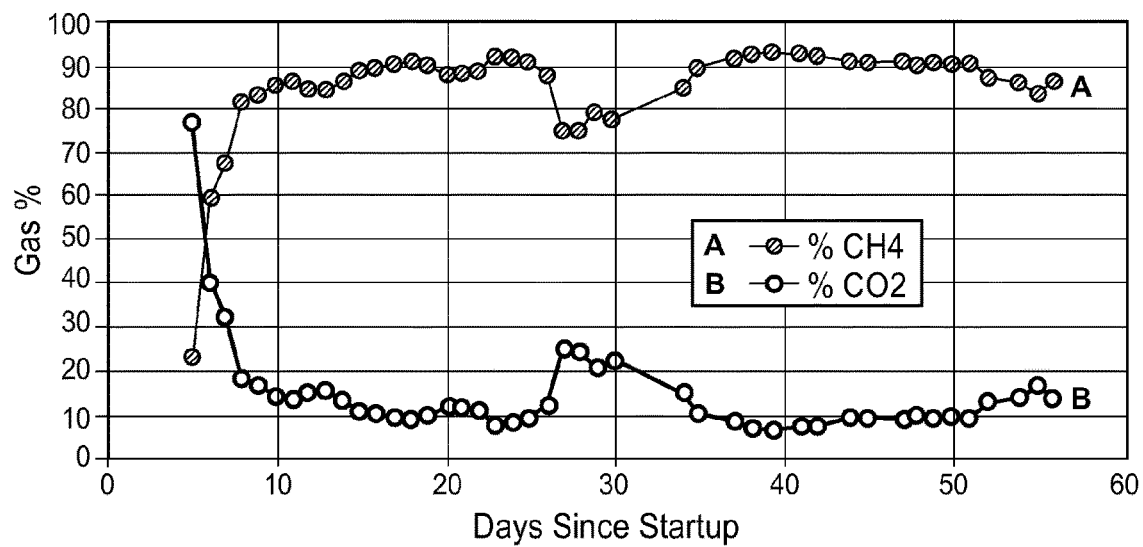
FIG. 9 is a graph illustrating methane and carbon dioxide content in biogas as a function of time since startup for a bioreactor insert apparatus and corresponding bioreactor according to the disclosure.
Figure 10:
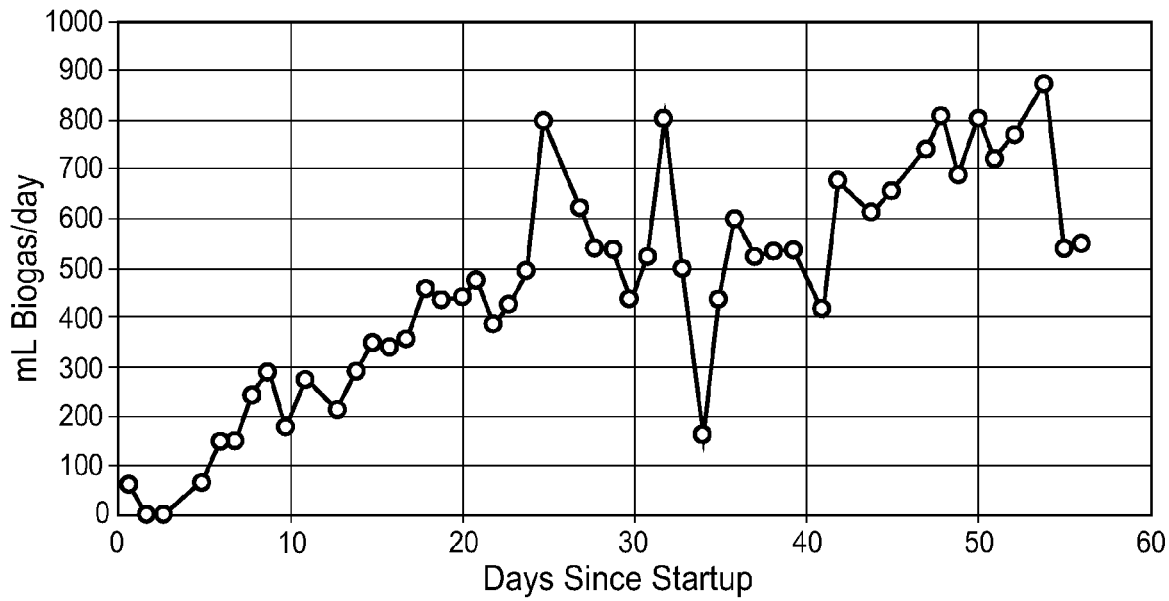
FIG. 10 is a graph illustrating biogas production rate as a function of time since startup for a bioreactor insert apparatus and corresponding bioreactor according to the disclosure.

Biological Performance and Biogas Production: Organics degradation in the reactor was assessed via VFA and COD data. Initially, VFA accumulated in the reactor to concentrations over 150 mg/L O$_2$ (COD eq.), but levels generally decreased past day 27 (FIG. 8). During this startup period, total COD removal increased from 20% to 72% and was expected to continue to increase as the microbial community adapted to the bioreactor operating conditions. The biogas methane content reached 90% after 16 days and remained around 90% thereafter (FIG. 9). The bioreactor lid was temporarily opened (at about day 26) to address clogging in tubing, which in turn led to a decrease in methane content and increase in carbon dioxide (FIG. 9). The biogas production rate increased steadily after reactor startup, albeit with some fluctuations (FIG. 10). The increase in biogas production indicates an increasingly larger proportion of influent organics being converted to methane and carbon dioxide.

Figure 11:
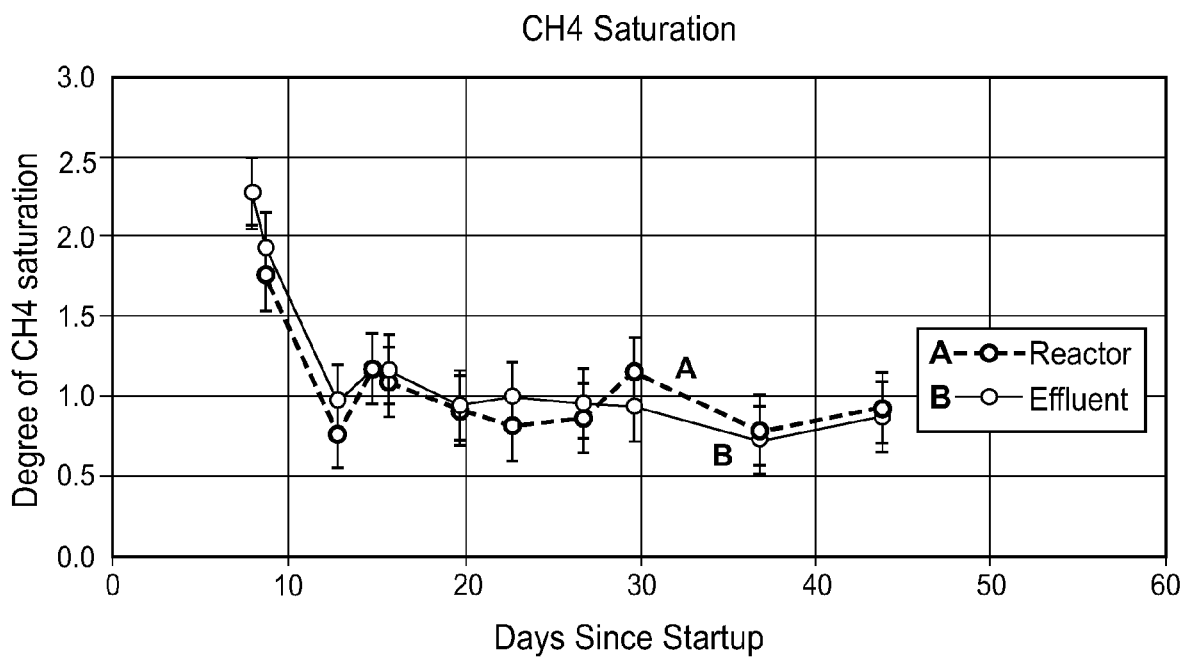
FIG. 11 is a graph illustrating degree of dissolved methane saturation as a function of time since startup for a bioreactor insert apparatus and corresponding bioreactor according to the disclosure.

Methane Solubility: A goal of the bioreactor design was to promote methanogenic activity on the influent branches and limit methanogenic activity on the permeating branches. By doing so, the dissolved methane content in the reactor would be provided time to approach and/or reach equilibrium with the reactor headspace, corresponding to a relative degree of saturation of 1. Saturation degrees above 1 (i.e., oversaturation) represent more dissolved methane in the liquid phase than would be predicted by equilibrium. Oversaturation is undesirable because the energy potential in the dissolved methane cannot be utilized as it could be in the gaseous phase and because the dissolved methane would otherwise be released into the atmosphere as a potent greenhouse gas. After 13 days, dissolved methane concentrations had reduced to reach relative degrees of saturation of essentially 1, and remained at 1 thereafter, indicating that the bioreactor and insert design successfully to mitigate dCH4 oversaturation (FIG. 11).

Figure 12:
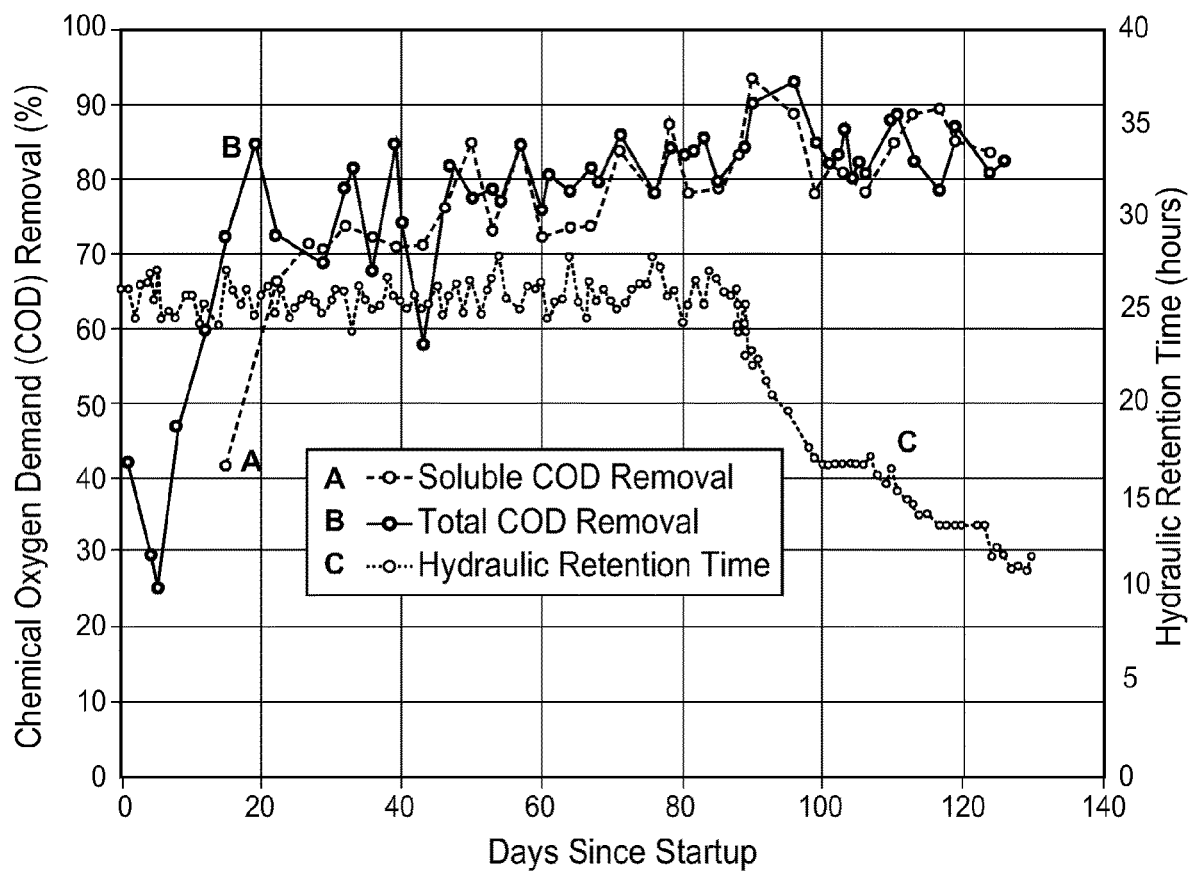
FIG. 12 is a graph illustrating degree of chemical oxygen demand (COD) removal and hydraulic retention time (HRT) as a function of time since startup for a bioreactor insert apparatus and corresponding bioreactor according to the disclosure.

Extended Operation and HRT: An advantage of the bioreactor design is that it is capable of operation for extended periods while achieving both high volumetric throughput (e.g., as reflected by a low HRT value) and effective organics degradation (e.g., as reflected by COD data). FIG. 12 illustrates operation of a bioreactor according to the disclosure over an extended period of 130 days after startup. The HRT remained steady at a value of about 24-28 hr for 90 days, and the HRT was reduced to values as low as about 10-14 hr for operational times up to 130 days. Soluble and total COD removal were consistently high over all HRT values, ranging from about 70-90% removal during operational times from about 20 to 130 days (e.g., after an initial startup transient).

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expressions "coupled," "connected," and "communication," along with their derivatives. For example, some embodiments may be described using the terms "coupled" or "in communication" to indicate that two or more elements are in direct physical or electrical contact. The terms "coupled" or "in communication," however, may also mean that two or more elements are not in direct contact with each other, but yet still co-operate or interact with each other, for example with fluids (e.g., liquid and/or gas, optionally with dispersed solids therein) being able to flow between the elements, such as via suitable piping or other conduits. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

Figure Parts List
  100 bioreactor insert apparatus
  102 first (or inlet/influent/feed) structure
  104 second (or outlet/effluent/permeate) structure
  110 inlet volume
  112, 112A cylindrical tube, tube axis/centerline
  114, 114A first fluid inlet, fresh feed inlet
  120 outlet volume
  122, 122A annular or cylindrical tube, tube axis/centerline
  124, 124A first fluid outlet, recycle portion of effluent
  130 exit volumes
  132 exit tubes
  134 exit biofilm support (e.g., mesh)
  136 exit biofilm
  138 exit biofilm seed/precursor
  140 recirculation volume
  142 recirculation tubes
  144 recirculation biofilm support (e.g., mesh)
  146 recirculation biofilm
  148 recirculation biofilm seed/precursor
  150 external volume
  200 bioreactor
  210, 210A, 210B reaction vessel
  220 interior reaction volume
  230 headspace
  234 gas outlet
  300 reaction medium
  400 separation membrane
  402, 404, 406 membrane inlet, retentate outlet, permeate outlet

REFERENCES

1. McCarty, P. L., Bae, J. & Kim, J. Domestic Wastewater Treatment as a Net Energy Producer—Can This be Achieved? Environ. Sci. Technol. 45,7100-7106 (2011).
2. Smith, A. L. et al. Navigating Wastewater Energy Recovery Strategies: A Life Cycle Comparison of Anaerobic Membrane Bioreactor and Conventional Treatment Systems with Anaerobic Digestion. Environ. Sci. Technol. 48,5972-5981 (2014).
3. Hu, Y., Wang, X. C., Ngo, H. H., Sun, Q. & Yang, Y. Anaerobic dynamic membrane bioreactor (AnDMBR) for wastewater treatment: A review. Bioresour. Technol. 247, 1107-1118 (2018).
4. Skouteris, G., Hermosilla, D., Lopez, P., Negro, C. & Blanco, A. Anaerobic membrane bioreactors for wastewater treatment: A review. Chem. Eng. J. 198-199,138-148 (2012).
5. Smith, A. L., Skerlos, S. J. & Raskin, L. Membrane biofilm development improves COD removal in anaerobic membrane bioreactor wastewater treatment. Microb. Biotechnol. 8, 883-894 (2015).
6. Buntner, D., Sanchez, A. S. & Garrido, J. M. Three stages MBR (methanogenic, aerobic biofilm and membrane filtration) for the treatment of low-strength wastewaters. Water Sci. Technol. 64,397-402 (2011).
7. Ersahin, M. E. et al. A review on dynamic membrane filtration: Materials, applications and future perspectives. Bioresour. Technol. 122,196-206 (2012).
8. Xie, Z., Wang, Z., Wang, Q., Zhu, C. & Wu, Z. An anaerobic dynamic membrane bioreactor (AnDMBR) for landfill leachate treatment: Performance and microbial community identification. Bioresour. Technol. 161,29-39 (2014).
9. Guan, D. et al. Pilot trial study of a compact macro-filtration membrane bioreactor process for saline wastewater treatment. Water Sci. Technol. 70,120-126 (2014).
10. Wang, Y.-K., Sheng, G.-P., Li, W.-W. & Yu, H.-Q. A pilot investigation into membrane bioreactor using mesh filter for treating low-strength municipal wastewater. Bioresour. Technol. 122,17-21 (2012).
11. Lovley, D. R. Happy together: microbial communities that hook up to swap electrons. ISME J. 11,327-336 (2017).
12. Li, Y., Zhang, Y., Yang, Y., Quan, X. & Zhao, Z. Potentially direct interspecies electron transfer of methanogenesis for syntrophic metabolism under sulfate reducing conditions with stainless steel. Bioresour. Technol. 234,303-309 (2017).
13. Leng, L. et al. A review on the bioenergetics of anaerobic microbial metabolism close to the thermodynamic limits and its implications for digestion applications. Bioresour. Technol. (2017). doi:10.1016/j.biortech.2017.09.103.
14. Guan, D., Dai, J., Watanabe, Y. & Chen, G. Changes in the physical properties of the dynamic layer and its correlation with permeate quality in a self-forming dynamic membrane bioreactor. Water Res. 140, 67-76 (2018).
15. Daigger, G. T. Evolving Urban Water and Residuals Management Paradigms: Water Reclamation and Reuse, Decentralization, and Resource Recovery. (2009). doi: info:doi/10.2175/106143009X425898
16. Skouteris, G., Hermosilla, D., Lopez, P., Negro, C. & Blanco, A. Anaerobic membrane bioreactors for wastewater treatment: A review. Chem. Eng. J. 198-199, 138-148 (2012).
17. Smith, A. L., Stadler, L. B., Love, N. G., Skerlos, S. J. & Raskin, L. Perspectives on anaerobic membrane bioreactor treatment of domestic wastewater: A critical review. Bioresour. Technol. 122, 149-159 (2012).
18. Ozgun, H. et al. A review of anaerobic membrane bioreactors for municipal wastewater treatment: Integration options, limitations and expectations. Sep. Purif. Technol. 118, 89-104 (2013).
19. Lin, H. et al. A review on anaerobic membrane bioreactors: Applications, membrane fouling and future perspectives. Desalination 314, 169-188 (2013).
20. Shin, C. & Bae, J. Current status of the pilot-scale anaerobic membrane bioreactor treatments of domestic wastewaters: A critical review. Bioresour. Technol. (2017). doi:10.1016/j.biortech.2017.09.002
21. Lei, Z. et al. Application of anaerobic membrane bioreactors to municipal wastewater treatment at ambient temperature: a review of achievements, challenges, and perspectives. Bioresour. Technol. (2018). doi:10.1016/j.biortech.2018.07.050
22. L. Smith, A., J. Skerlos, S. & Raskin, L. Anaerobic membrane bioreactor treatment of domestic wastewater at psychrophilic temperatures ranging from 15° C. to 3° C. Environ. Sci. Water Res. Technol. 1, 56-64 (2015).

What is claimed:

1. A bioreactor insert apparatus for reaction medium circulation, biofilm support, and biological treatment, the apparatus comprising:
an inlet volume in fluid communication with a first fluid inlet;
an outlet volume in fluid communication with a first fluid outlet;
a plurality of modular exit volumes, each exit volume being in fluid communication with the inlet volume and comprising at least one exit biofilm support disposed at a boundary between the exit volume and an external volume outside the bioreactor insert apparatus, wherein: the exit biofilm support is adapted to promote growth, attachment, and metabolism of microorganisms in the form of a biofilm thereon, and the exit biofilm support is adapted to permit fluid and solid transport across the exit biofilm support and between the exit volume and the external volume, and each modular exit volume is adapted to be selectively replaced with a different modular exit volume having at least one of a different geometry and a different material relative to the replaced modular exit volume; and
a plurality of modular recirculation volumes, each recirculation volume being in fluid communication with the outlet volume and comprising at least one recirculation biofilm support disposed at a boundary between the recirculation volume and the external volume outside the bioreactor insert apparatus, wherein: the recirculation biofilm support is adapted to promote growth, attachment, and metabolism of microorganisms in the form of a biofilm thereon, the recirculation biofilm support is adapted to permit fluid and solid transport across the recirculation biofilm support and between the recirculation volume and the external volume, and each modular recirculation volume is adapted to be selectively replaced with a different modular recirculation volume having at least one of a different geometry and a different material relative to the replaced modular recirculation volume;
wherein a ratio ($A/V_A$) of total surface area (A) of all biofilm supports combined to bioreactor insert apparatus volume ($V_A$) is at least 1 $m^{-1}$.

2. The apparatus of claim 1, wherein the bioreactor insert apparatus comprises:
a first structure comprising the inlet volume and the plurality of exit volumes mounted thereto; and
a second structure comprising the outlet volume and the plurality of recirculation volumes mounted thereto; and
wherein the first structure and the second structure are separate structures with the exit volumes being in fluid communication with the recirculation volumes via the external volume.

3. The apparatus of claim 1, wherein the first fluid outlet is in fluid communication with the first fluid inlet.

4. The apparatus of claim 1, wherein the apparatus comprises at least 10 exit volumes.

5. The apparatus of claim 1, wherein the apparatus comprises at least 10 recirculation volumes.

6. The apparatus of claim 1, wherein the biofilm support is in the form of a mesh.

7. The apparatus of claim 1, wherein the biofilm support comprises an electrically conductive material.

8. The apparatus of claim 1, wherein:
at least one of the insert apparatus and the biofilm support comprises an electrically resistive material, and the electrically resistive material is in electrical connection with a power source adapted to supply electrical current to the electrically resistive material and to heat the electrically resistive material.

9. The apparatus of claim 1, wherein the bioreactor insert apparatus or at least one component thereof has been formed by a 3D printing process.

10. The apparatus of claim 1, further comprising biofilms adhered to the biofilm supports, the biofilms comprising a community of microorganisms collectively having biological activity.

11. The apparatus of claim 1, further comprising a biofilm seed adhered to the biofilm support, the biofilm seed comprising a water-soluble adhesive matrix and a community of microorganisms as a biofilm precursor distributed throughout the matrix.

12. The apparatus of claim 1, wherein:
the inlet volume is defined by an inlet conduit in fluid communication with the first fluid inlet;
the outlet volume is defined by an outlet conduit in fluid communication with the first fluid outlet;
the modular exit volumes are defined by one or more modular exit modules each comprising a plurality of exit conduits in fluid communication with the inlet conduit; and
the modular recirculation volumes are defined by one or more modular recirculation modules each comprising a plurality of recirculation conduits in fluid communication with the outlet conduit.

13. The apparatus of claim 1, wherein:
each modular exit volume is adapted to be selectively replaced with the different modular exit volume having the different geometry relative to the replaced modular exit volume; and
each modular recirculation volume is adapted to be selectively replaced with the different modular recirculation volume having the different geometry relative to the replaced modular recirculation volume.

14. The apparatus of claim 1, wherein:
each modular exit volume is adapted to be selectively replaced with the different modular exit volume having the different material relative to the replaced modular exit volume; and
each modular recirculation volume is adapted to be selectively replaced with the different modular recirculation volume having the different material relative to the replaced modular recirculation volume.

15. A bioreactor comprising:
a reaction vessel defining an interior reaction volume; and
a bioreactor insert apparatus mounted within the reaction vessel, the bioreactor insert apparatus comprising:
an inlet volume in fluid communication with a first fluid inlet;
an outlet volume in fluid communication with a first fluid outlet;
a plurality of modular exit volumes, each exit volume being in fluid communication with the inlet volume and comprising at least one exit biofilm support disposed at a boundary between the exit volume and an external volume outside the bioreactor insert apparatus, wherein: the exit biofilm support is adapted to promote growth, attachment, and metabolism of microorganisms in the form of a biofilm thereon, the exit biofilm support is adapted to permit fluid and solid transport across the exit biofilm support and between the exit volume and the external volume, and each modular exit volume is adapted to be selectively replaced with a different modular exit volume having at least one of a different geometry and a different material relative to the replaced modular exit volume; and
a plurality of modular recirculation volumes, each recirculation volume being in fluid communication with the outlet volume and comprising at least one recirculation biofilm support disposed at a boundary between the recirculation volume and the external volume outside the bioreactor insert apparatus, wherein: the recirculation biofilm support is adapted to promote growth, attachment, and metabolism of microorganisms in the form of a biofilm thereon, the recirculation biofilm support is adapted to permit fluid and solid transport across the recirculation biofilm support and between the recirculation volume and the external volume, and each modular recirculation volume is adapted to be selectively replaced with a different modular recirculation volume having at least one of a different geometry and a different material relative to the replaced modular recirculation volume;
wherein the external volume corresponds to a portion of the interior reaction volume outside the bioreactor insert apparatus.

16. The bioreactor of claim 15, wherein a ratio ($A/V_A$) of total surface area (A) of all biofilm supports combined to bioreactor insert apparatus volume ($V_A$) is at least $1\ m^{-1}$.

17. The bioreactor of claim 15, wherein the bioreactor insert apparatus is rotatably mounted within the reaction vessel.

18. The bioreactor of claim 15, further comprising a bioreactor gas outlet in fluid communication with a headspace portion of the interior reaction volume.

19. The bioreactor of claim 15, further comprising attachment media for microbial growth.

20. The bioreactor of claim 15, further comprising a membrane filtration unit comprising:
a separation membrane,
a membrane inlet in fluid communication with the first fluid outlet and a first side of the separation membrane,
a membrane retentate outlet in fluid communication with the first fluid inlet and the first side of the separation membrane, and
a membrane permeate outlet in fluid communication with a second side of the separation membrane.

21. A method for forming a bioreactor product, the method comprising:
providing a bioreactor according to claim 14, wherein:
the bioreactor insert apparatus further comprises biofilms adhered to the biofilm supports, the biofilms having biological activity,
an aqueous reaction medium at least partially fills the interior reaction volume and the bioreactor insert apparatus, and
suspended microorganisms are present in the aqueous reaction medium;
feeding an influent stream comprising one or more reactants for conversion to the bioreactor insert apparatus via the first fluid inlet;
circulating the influent stream through the inlet volume, into the exit volumes, through the exit biofilm supports and biofilms thereon, into the external volume, through the recirculation biofilm supports and biofilms thereon, into the recirculation volumes, into the outlet volume, and through the first fluid outlet; and
converting the one or more influent reactants to a product.

22. The method of claim 21, wherein at least 50% of total microorganisms in the bioreactor are incorporated into the biofilms.

23. The method of claim 21, wherein the biofilms have methanogenic activity.

24. The method of claim 23, wherein aqueous fluid removed through the first fluid outlet comprises dissolved methane at a concentration in a range of 50% to 150% relative to the equilibrium concentration of methane in water.

25. The method of claim 21, wherein the biofilms comprising a community of anaerobic microorganisms.

26. The method of claim 21, wherein the biofilms comprising a community of aerobic microorganisms.

27. The method of claim 21, wherein the biofilms comprising a community of anoxic microorganisms.

28. The method of claim 21, comprising operating the bioreactor at a temperature in a range of 1° C. to 60° C.

29. The method of claim 21, where the bioreactor further comprises attachment media for microbial growth suspended in the aqueous reaction medium.

30. The method of claim 21, comprising operating the bioreactor at a hydraulic retention time (HRT) in a range of 2 hr to 40 hr.

31. The method of claim 21, further comprising at least one of:

selectively replacing at least one modular exit volume with a different modular exit volume having a different geometry relative to the replaced modular exit volume; and selectively replacing at least one modular recirculation volume with a different modular recirculation volume having a different geometry relative to the replaced modular recirculation volume.

32. The method of claim 21, further comprising at least one of:

selectively replacing at least one modular exit volume with a different modular exit volume having a different material relative to the replaced modular exit volume; and selectively replacing at least one modular recirculation volume with a different modular recirculation volume having a different material relative to the replaced modular recirculation volume.

* * * * *